US009281206B2

(12) United States Patent
Jin et al.

(10) Patent No.: US 9,281,206 B2
(45) Date of Patent: Mar. 8, 2016

(54) SEMICONDUCTOR PROCESSING BY MAGNETIC FIELD GUIDED ETCHING

(71) Applicant: The Regents of the University of California, Oakland, CA (US)

(72) Inventors: Sungho Jin, San Diego, CA (US);
Young Oh, San Diego, CA (US);
Chulmin Choi, San Diego, CA (US);
Dae-Hoon Hong, Fremont, CA (US);
Tae Kyoung Kim, La Jolla, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 33 days.

(21) Appl. No.: 14/351,690

(22) PCT Filed: Oct. 12, 2012

(86) PCT No.: PCT/US2012/060143
§ 371 (c)(1),
(2) Date: Apr. 14, 2014

(87) PCT Pub. No.: WO2013/056186
PCT Pub. Date: Apr. 18, 2013

(65) Prior Publication Data
US 2014/0256078 A1    Sep. 11, 2014

Related U.S. Application Data

(60) Provisional application No. 61/546,542, filed on Oct. 12, 2011.

(51) Int. Cl.
*H01L 21/302* (2006.01)
*H01L 21/306* (2006.01)
(Continued)

(52) U.S. Cl.
CPC ............ *H01L 21/30608* (2013.01); *B28D 5/00* (2013.01); *B81C 1/00111* (2013.01);
(Continued)

(58) Field of Classification Search
None
See application file for complete search history.

(56) References Cited

U.S. PATENT DOCUMENTS 8,278,191 B2 * 10/2012 Hildreth et al. ............... 438/460
2008/0272299 A1 * 11/2008 Jin et al. ........................ 250/310
(Continued)

OTHER PUBLICATIONS

Lee, S. J., Authorized Officer, Korean Intellectual Property Office, International Search Report, International Patent Application No. PCT/US2012/060143, Mar. 18, 2013, 7 pages.
(Continued)

*Primary Examiner* — David E Graybill
(74) *Attorney, Agent, or Firm* — Perkins Coie LLP

(57) ABSTRACT

Methods, systems, and devices are described for slicing and shaping materials using magnetically guided chemical etching. In one aspect, a method includes forming a pattern on a substrate by a mask, depositing a catalytic etcher layer on the patterned substrate, a magnetic guide layer on the etcher layer, and a protection layer on the guide layer, etching the substrate by applying an etching solution to the substrate that chemically reacts with the etcher layer and etches material from the substrate at exposed regions not covered by the mask, steering the composite etching structure into the substrate during the etching by an applied magnetic field that creates a force on the guide layer to direct the etching, in which the steering defines the shape of the sliced regions of the etched substrate, and removing the etched material, the mask, and the composite etching structure to produce a sliced material structure.

38 Claims, 19 Drawing Sheets

(51) Int. Cl.
| | |
|---|---|
| B28D 5/00 | (2006.01) |
| H01L 21/67 | (2006.01) |
| B82Y 30/00 | (2011.01) |
| B81C 1/00 | (2006.01) |
| H01L 31/0352 | (2006.01) |
| H01L 31/0236 | (2006.01) |
| H01L 31/068 | (2012.01) |
| H01L 31/18 | (2006.01) |
| A61M 37/00 | (2006.01) |

(52) U.S. Cl.
CPC ............ *B81C1/00515* (2013.01); *B82Y 30/00* (2013.01); *H01L 21/30604* (2013.01); *H01L 21/67086* (2013.01); *H01L 31/02366* (2013.01); *H01L 31/03529* (2013.01); *H01L 31/035209* (2013.01); *H01L 31/035281* (2013.01); *H01L 31/068* (2013.01); *H01L 31/1804* (2013.01); *A61M 2037/0046* (2013.01); *A61M 2037/0053* (2013.01); *B81B 2201/055* (2013.01); *Y02E 10/547* (2013.01)

(56) References Cited

U.S. PATENT DOCUMENTS

| | | | | |
|---|---|---|---|---|
| 2010/0229265 | A1* | 9/2010 | Jin et al. ......................... | 850/60 |
| 2010/0248449 | A1* | 9/2010 | Hildreth et al. ............... | 438/460 |
| 2014/0256078 | A1* | 9/2014 | Jin et al. ......................... | 438/57 |

OTHER PUBLICATIONS

Huang, M.-J. et al., "PMMA nanocolumn array fabricated by catalytic etching and nanomolding technique", Microelectronic Engineering, vol. 88, 2011, pp. 2576-2579.
Choi, W.K. et al., "Synthesis of Silocon Nanowires and Nanofin Arrays Using Interference Lithography and Catalytic Etching", Nano Letters, vol. 8, 2008, pp. 3799-3802.
Lee, J.P. et al., Patterning of various silicon structures via polymer lithography and catalytic chemical etching, Nanotechnology, vol. 22, May 2011, 6 pages.
Panda, S. et al., "Etching High Aspect Ratio Silicon Trenches", J. Electrochem. Soc., 150 (10), 2003, pp. G612-G616.
Rangelow, I., "Critical tasks in high aspect ratio silicon dry etching for microelectromechanical systems", J. Vac. Sci. Technol., A 21, 1550, 2003, pp. 1550-1562.
Li, X. et al., "Metal-assisted chemical etching in HF/H 2 O 2 produces porous silicon", Appl. Phys. Lett. 77, No. 16, 2000, pp. 2572-2574.
Hadjersi, T. et al., "Blue luminescence from porous layers produced by metal-assisted chemical etching on low-doped silicon", Vacuum 80, 2005, pp. 366-370.
Gorostiza, P. et al., "Simultaneous platinum deposition and formation of a photoluminescent porous silicon layer", J. Electroanal.Chem., 469, 1999, pp. 48-52.
Yae, S. et al., "Formation of porous silicon by metal particle enhanced chemical etching in HF solution and its application for efficient solar cells", Electrochem., Commun., 5, 2003, pp. 632-636.
Tsujino, K. et al., "Texturization of multicrystallline silicon wafers for solar cells by chemical treatment using metallic catalyst", Sol. Energy Mater. Sol. Cell, 90, 2006 pp. 100-110.
Zhao, J. et al., "19.8% efficient 'honeycomb' textured multicrystalline and 24.4% monocrystalline silicon solar cells", Appl. Phys. Lett., Vo. 73, No. 14, 1998, pp. 1991-1993.
Levy-Clement, C. et al., "Macropore formation on p-type multicrystalline silicon and solar cells", Phys. Stat. Sol. A, 197, No. 1, 2003, pp. 27-33.
Hsu, D.S. et al., "Conformal chemical beam deposition of thin metal film for fabricating high density trench capacitor cells", Appl. Phys. Lett. 63, 159, 1993, pp. 159-161.
Cruz, S. et al., "Fabrication and Optimization of Porous Silicon Substrates for Diffusion Membrane Applications", J. Electrochem. Soc., 152, 6, 2005, pp. C418-C424.
Takahashi, K. et al. "Current Status of Research and Development for Three-Dimensional Chip Stack Technology", Jpn. J. Appl. Phys., vol. 40 (2001), pp. 3032-3037.
Satoh, A., "Wiring of Bumpless, Three-dimensional Integrated Si Wafers Block Using Through-hole Interconnections", Jpn. J. Appl. Phys., vol. 40 (2001), pp. 4774-4780.
Burkett, S. L. et al., "Advanced processing techniques for through-wafer interconnects", J. Vac. Sci. Technol. B 22 (1), 2004, pp. 248-256.
Lee, C.-L. et al., "Pore formation in silicon by wet etching using micrometer-sized metal particles as catalysts", J. Mater. Chem., 18, 2008, pp. 1015-1020.
Tsujino, K. et al., "Morphology of nanoholes formed in silicon by wet etching solutions containing HF and $H_2O_2$ at different concentrations using silver nanoparticles as catalysts", Electrochim. Acta, 53, 2007, pp. 28-34.
Tsujino, K. et al., "Boring Deep Cylindrical Nanoholes in Silicon Using Silver Nanoparticles as a Catalyst", Adv. Mater. 2005, 17, No. 8, pp. 1045-1047.
Tsujino, K. et al., "Helical Nanoholes Bored in Silicon by Wet Chemical Etching Using Platinum Nanoparticles as Catalyst", Electrochem. Solid-State Lett., 8 (12), 2005, pp. C193-C195.
Lee . W. et al., "Individually addressable epitaxial ferroelectric nanocapacitor arrays with near Tb $inch^{-2}$ density", U. Nature Nanotech. vol. 3, 2008, pp. 402-408.
Chong, A.S.M. et al., "Soft Imprinting: Creating Highly Ordered Porous Anodic Alumina Templates on Substrates for Nanofabrication", Adv. Funct. Mater. 2007, 17, pp. 1629-1635.
Peng, K.-Q. et al., "Silicon Nanowires for Photovoltaic Solar Energy Conversion", Adv. Mater. 23, 2011, pp. 198-21.
Sun, Y. et al., "Inorganic Semiconductors for Flexible Electronics," Advanced Materials 19, 2007, pp. 1897-1916.
Kim, D.-H. et al., "Stretchable and Foldable Silicon Integrated Circuits," Science 320, 2008, pp. 507-511.
Baca, A.J. et al., "Semiconductor Wires and Ribbons for High-Performance Flexible Electronics," Angewandte Chemie International Edition 47, 2008, pp. 5524-5542.
Ko, H.C. et al., "A Hemispherical Electronic Eye Camera Based on Compressible Silicon Optoelectronics," Nature 454, 2008, pp. 748-753.
Raut, H.K. et al., "Anti-reflective coatings: A critical, in-depth review", Energy Environ. Sci. 2011, 4, pp. 3779-3804.
Jain, K.K., "Commercial potential of RNAi", Mol Biosyst. 2006, 2, pp. 523-526.
Shalek, A.K. et al., "Vertical silicon nanowires as a universal platform for delivering biomolecules into living cells", Proc Natl Acad Sci., vol. 107, No. 5, 2010, pp. 1870-1875.

\* cited by examiner

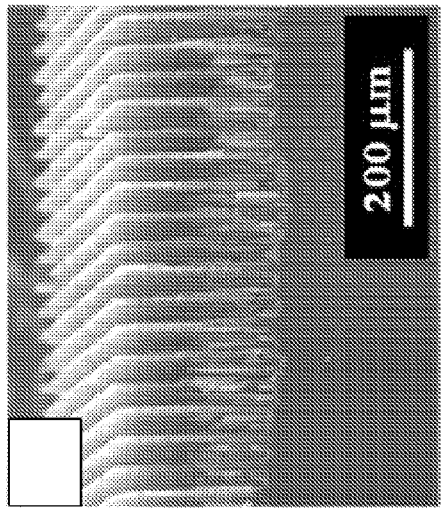
FIG. 6B
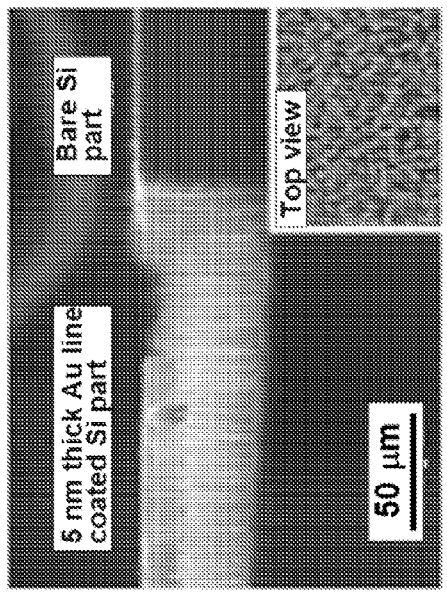
FIG. 6A
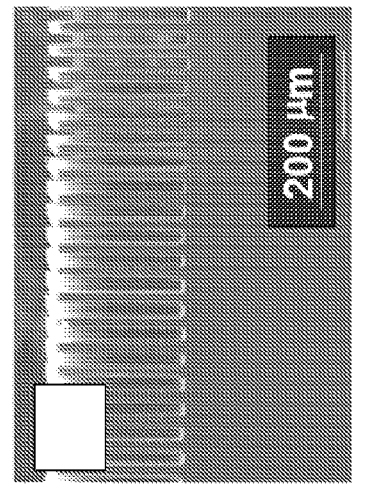
FIG. 6E
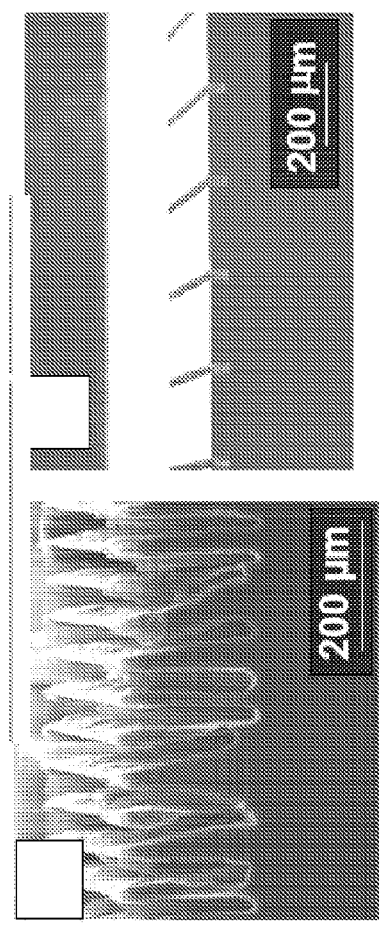
FIG. 6D
FIG. 6C

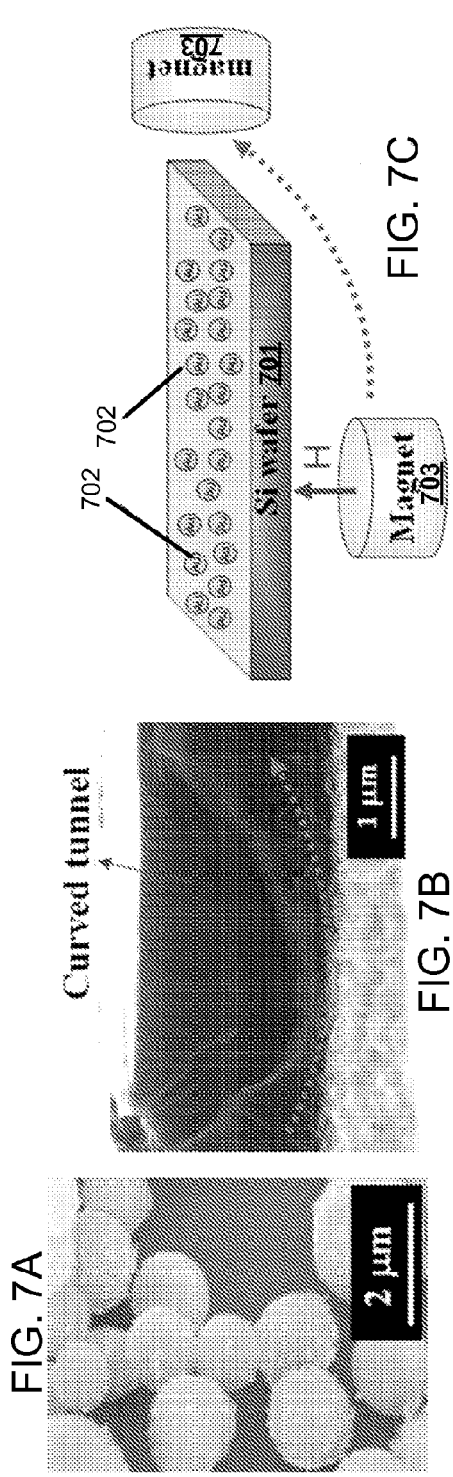
FIG. 7A
FIG. 7B
FIG. 7C
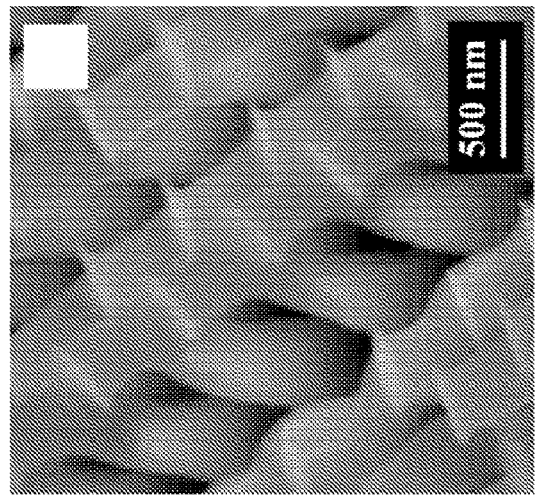
FIG. 7F
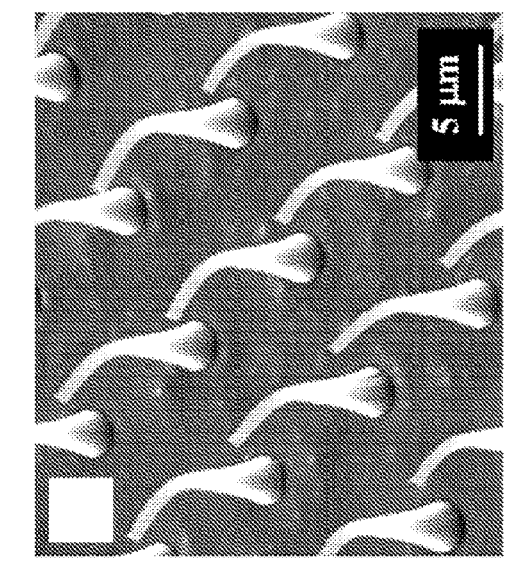
FIG. 7E
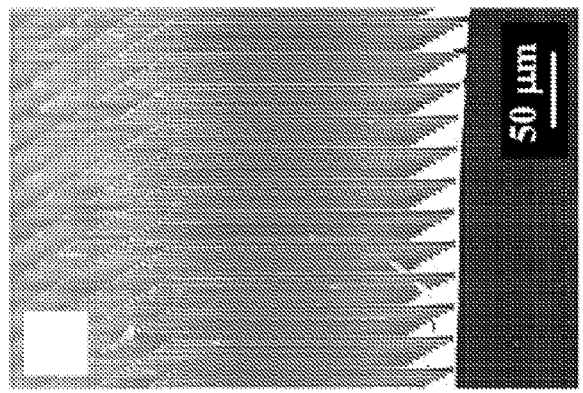
FIG. 7D

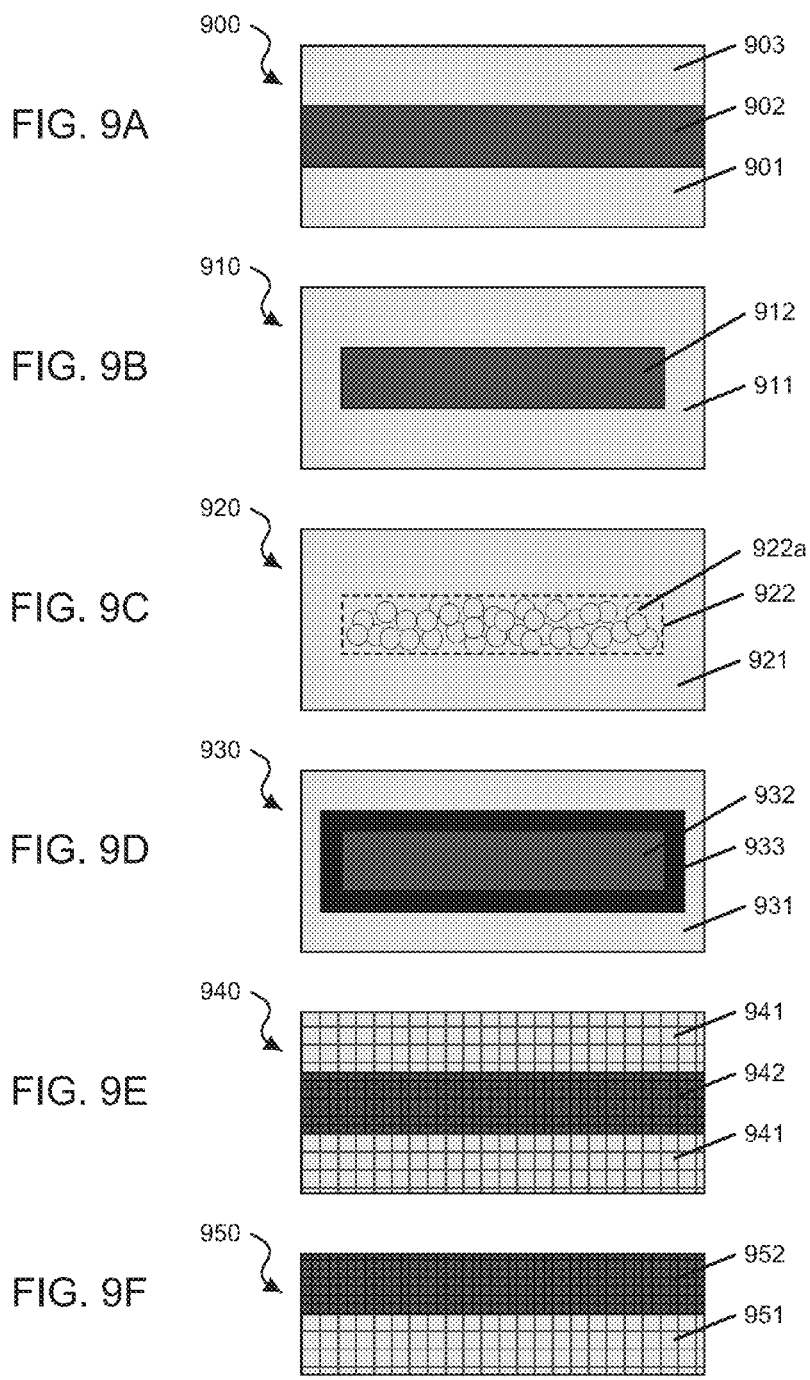

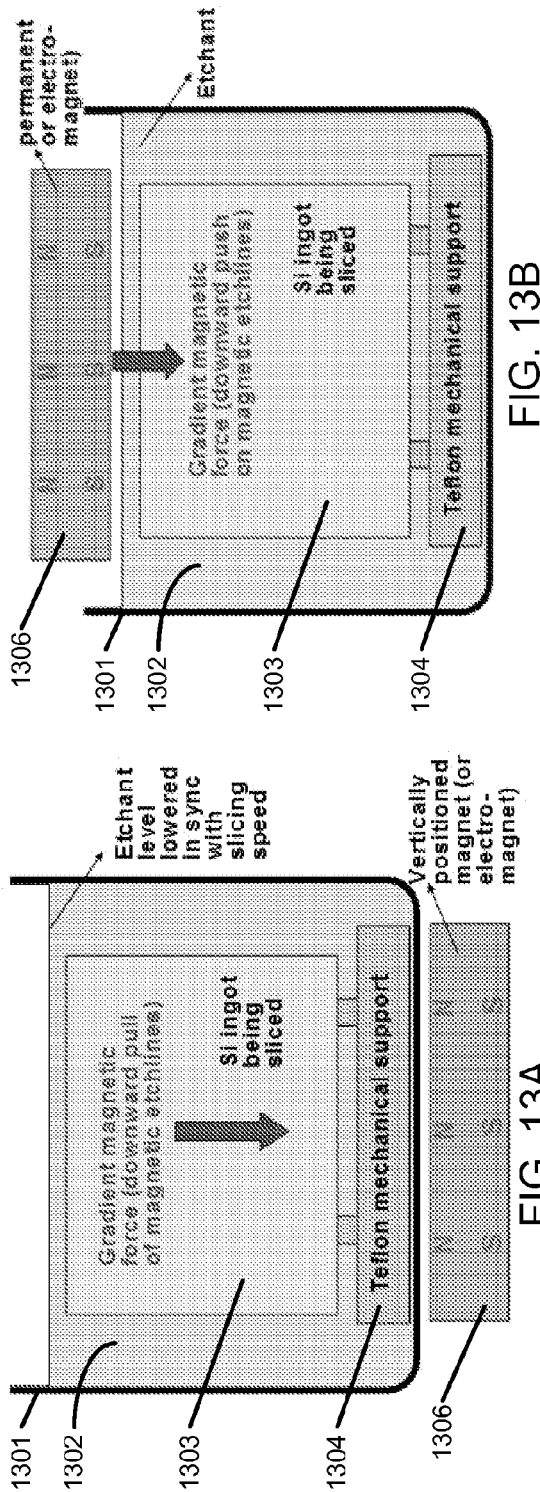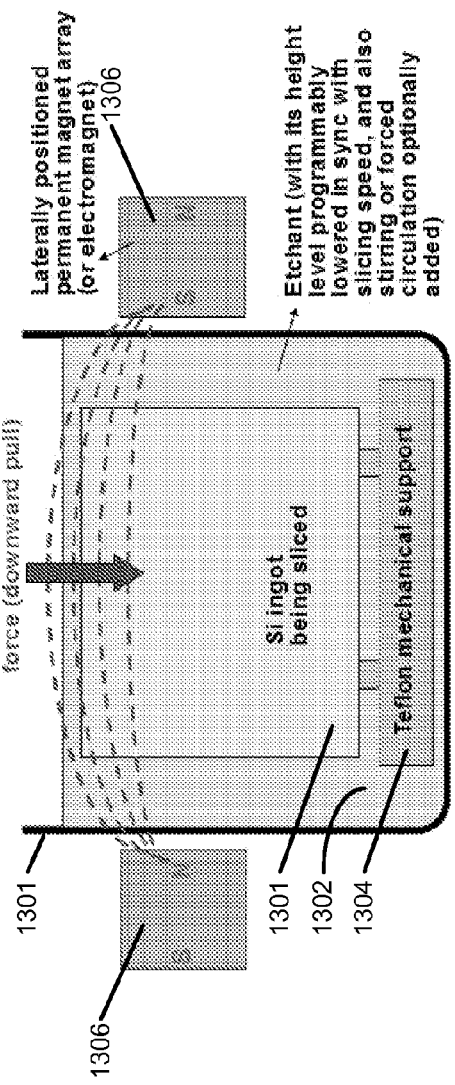
FIG. 13A
FIG. 13B
FIG. 13C

SEMICONDUCTOR PROCESSING BY MAGNETIC FIELD GUIDED ETCHING

CROSS REFERENCE TO RELATED APPLICATIONS

This application is a 35 USC 371 National Stage application of International Application No. PCT/US2012/060143 filed Oct. 12, 2012, which further claims the benefit of priority to U.S. provisional application No. 61/546,542 entitled "ARTICLE COMPRISING THIN SLICED SEMICONDUCTORS BY MAGNETIC-FIELD-GUIDED ETCHING, METHOD OF SLICING, AND DEVICE APPLICATIONS" filed on Oct. 12, 2011, the disclosures of which are incorporated by reference as part of this document.

TECHNICAL FIELD

This patent document relates to nanoscale semiconductor materials.

BACKGROUND

Nanotechnology provides techniques or processes for fabricating structures, devices, and systems with features at a molecular or atomic scale, e.g., structures in a range of one to hundreds of nanometers in some applications. For example, nano-scale devices can be configured to sizes similar to some large molecules, e.g., biomolecules such as enzymes. Nano-sized materials used to create a nanostructure, nanodevice, or a nanosystem that can exhibit various unique properties that are not present in the same materials at larger dimensions and such unique properties can be exploited for a wide range of applications.

SUMMARY

Systems, devices, and techniques are disclosed for magnetically guided directional electroless etching to slice and shape materials, e.g., including parallel chemical slicing to form thin-sliced or thin-patterned semiconductors. Also, various applications of such thin semiconductors are described.

The subject matter described in this patent document can be implemented in specific ways that provide one or more of the following features. For example, implementations of the described magnetically guided parallel chemical slicing techniques can reduce or prevent mechanical damages to the silicon and increase the throughput and productivity in fabricating lower cost devices. For example, implementations of the magnetically guided slicing techniques can produce thin-sliced semiconductors that include silicon (Si), germanium (Ge) or alloys containing Si and Ge, or other semiconductor materials. Also, the magnetically guided chemical etching techniques can be used to produce regularly or randomly positioned nanowires and microwires or nanopores and micropores. The magnetically guided etching can be fast and the direction of the chemical etching can maintain accurate vertical direction, or any selected angle direction if desired. For example, one or more ferromagnetic metal catalyst in a variety of configurations, e.g., including a parallel line array, can be placed on an exemplary material such as a Si block, and the applied magnetic field can accurately guide the direction of the vertical slicing without undesirable, off-axis slicing. The magnetostatic attractive force can also accelerate the descending speed of the catalyst lines for more rapid slicing speed.

For example, the disclosed methods can be implemented to produce thin silicon slices of various thicknesses at any crystallographic orientations, shaping of tall needles, producing zigzag geometries, and producing micro/nano-tunneling paths. For example, techniques are described that utilize magnetically guided electroless etching for shaping of unconventional Si configurations. One of the many advantages of the disclosed processing techniques is the substantial reduction of Si materials cost that can be saved by implementing the disclosed techniques for producing devices for a variety of applications, including for photovoltaic solar cells. For example, massively parallel Si slicing is enabled and accelerated by magnetic guidance for significant reduction in solar grade Si material waste during saw cutting, and also the amount of Si usage in photovoltaic solar cells by convenient thinner-wafer fabrication.

For example, the disclosed techniques can be implemented such that thousands of parallel micrometer-wide lines of a composite etching structure (e.g., such as Au/Fe/Au trilayer) deposited on a polymer resist-patterned silicon wafer can simultaneously partition a large-area silicon wafer or silicon block vertically or along any desired angle following the applied magnetic field direction to produce as thin as ~5 μm thickness wafers. The magnetic material of the exemplary composite etching structure can include, but is not limited to, Fe, Co or CoPt thin film, sandwiched by protective Au thin films or other noble metal catalyst layers. For example, the magnetic gradient interaction of the sandwiched Fe layer with applied field can ensure a straight and vertical slicing at an accelerated rate, while Au surface enables catalytic electroless etching. A modified processing for creation of zigzag Si nanowires, tall and sharp needle arrays, and micro/nano-tunnel formation are also disclosed, which can be useful for a variety of device applications.

BRIEF DESCRIPTION OF THE DRAWINGS

FIGS. 6A-6E show SEM micrographs of various implementations of Si etching.

FIGS. 7A-7F shows SEM images and schematic illustrations of nonconventional geometries of silicon materials fabricated by implementing the disclosed techniques.

FIGS. 9A-9F show schematics of various configurations of the exemplary composite etching structure.

FIGS. 13A-13C show schematics of various magnet positions for the exemplary magnetically guided electroless etching process.

Like reference symbols and designations in the various drawings indicate like elements.

DETAILED DESCRIPTION

Figure 1A:
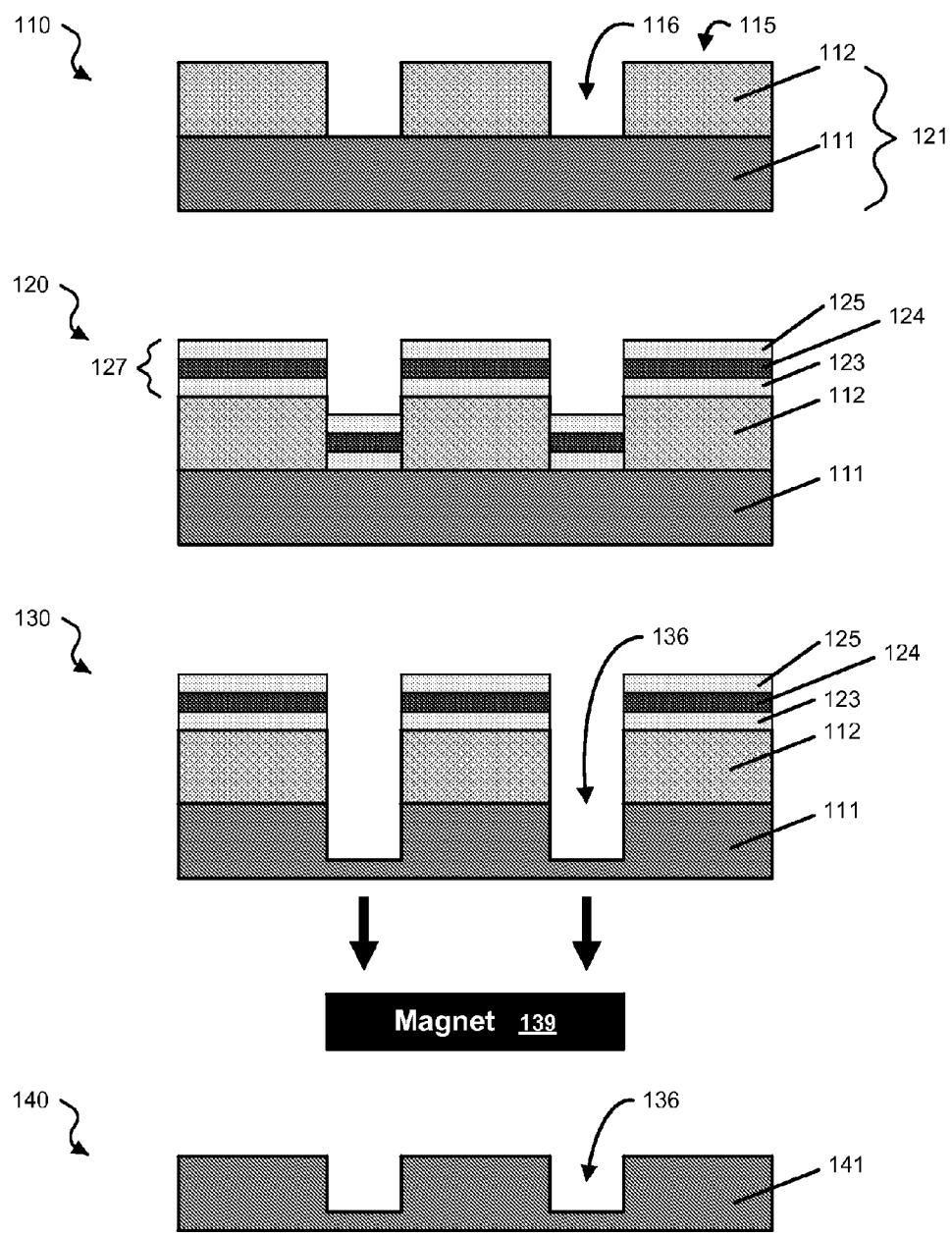
FIG. 1A shows a schematic illustration of a method to slice and shape a material by magnetically guided electroless etching.

Silicon is one of the most important materials in the semiconductor industry for electronics, micromachines, photovoltaic solar cells and other devices and products. Generally, a silicon wafer needs to be physically processed and shaped by processes including dry etching or wet etching for fabricating devices or circuits. For example, Si processing can involve various processing operations, including, e.g., cutting, grinding and blade dicing, or patterning for formation of specifically designed lines, grooves, pores or vertical columns on a silicon wafer. Certain processing operations, e.g., saw blade or laser cutting techniques, may cause damage to a silicon wafer under processing. Such damage can reduce the slicing throughput and a significant amount of silicon may be discarded during such process (e.g., from cutting with a blade having a finite thickness). These problems lower productivity and raise fabrication costs. Other processing techniques such as dry etching (or reactive ion etching) for producing a certain pattern or array on silicon in parallel fashion using photolithography masking may be slow and expensive. Wet etching processing techniques can be difficult to achieve a well-controlled etching and slicing of silicon at a desired speed.

Increasing demands for silicon for various applications, such as semiconductor devices and solar cells render the availability and pricing of the silicon material important practical issues. It would be highly desirable to provide silicon processing techniques that enable parallel Si slicing and patterning at a reduced cost and with minimal waste of the valuable Si material.

For example, about 90% of current photovoltaic cells is made of silicon. In fabrication of photovoltaic cells, silicon ingots need to be physically processed, for example, by slicing into wafers and implementing microscale/nanoscale geometrical changes for circuits and devices. For example, after a conventional wire sawing process to process a silicon ingot, only 45%-50% of the silicon feedstock ends up in a wafer. The remaining Si material is lost in the cutting process (Kerf loss) with the main loss as sawing slurry. Approximately half of the cost of existing high-efficiency solar cells based on crystalline Si wafers (e.g., having ~200 μm thickness) is derived from the cost of Si materials. If Si photovoltaic solar cells are to be a major ubiquitous factor as a world renewable energy technology, then Si materials usage efficiencies must be increased.

Systems, devices, and techniques are disclosed for magnetically guided directional electroless etching to slice and shape materials, including Si materials.

In one aspect, the disclosed technology includes a method for guided electroless etching. The method includes forming a pattern on a substrate by a mask that at least partially covers the surface of the substrate, depositing an etcher layer of a first catalyst material on the surface of the patterned substrate, a guide layer of a magnetic material on the etcher layer, and a protection layer of a second catalyst material on the guide layer, in which the etcher layer, guide layer and protection layer form a composite etching structure, etching the substrate by applying an etching solution to the substrate that chemically reacts with the etcher layer and etches material from the substrate at exposed regions not covered by the mask, steering the composite etching structure into the substrate during the etching by an applied magnetic field that creates a force on the guide layer to direct a direction of the etching, in which the steering defines the shape of the sliced regions of the etched substrate, and removing the etched material, the mask, and the composite etching structure from the substrate to produce a sliced material structure.

Electroless etching includes electrochemical oxidation without an external electrical potential. The exemplary magnetically guided directional electroless etching method can be implemented to slice and shape silicon into very thin wafers (e.g., 5-20 μm thin) along any crystal orientation, e.g., independent of the preferred crystallographic etch directions such as <100>. The method can be implemented to fabricate a zigzag bent Si microsheet or microwire array, e.g., by varying the magnetic field orientation during the etching process of the exemplary method, as well as gradually changing field directions for a guided micro-tunnel drilling into the Si material. For example, the described Si wafer slicing techniques can be used to create different orientations or bent/shaped microwires, which can be implemented in various new devices utilizing orientation-dependent electronic or photonic properties or metamaterial aspects.

Implementation of the disclosed Si processing techniques can enable a significant reduction of crystalline Si materials waste and usage in photovoltaic cells by at least a factor of ~5, and in some examples by at least a factor of ~10, which can lead to a large cost reduction of solar cells to enable accelerated widespread photovoltaic solar cell deployments. For example, such a reduction in crystalline Si materials usage can be accomplished by substantially reducing Kerf loss and by enabling silicon slicing of thinner wafers, e.g., on the order of ~5-20 μm thickness.

FIG. 1A shows a schematic illustration of a method to slice and shape a material (e.g., Si) by magnetically guided electroless etching. Four exemplary processing stages or processes 110, 120, 130 and 140 are illustrated.

The process 110 is performed to form a pattern on a substrate 111 (e.g., Si) by creating a pattern mask of a masking material 112 on the surface of the substrate 111. The pattern can include, e.g., line patterns, rectangle patterns, circular patterns, curved patterns, or irregular patterns. The exemplary illustration of the process 110 shows a line pattern of the masking material 112 on the substrate 111 to form a patterned substrate 121. The pattern formed on the patterned substrate 121 includes masked regions 115 that include the masking material 112 on the substrate 111 and unmasked regions 116 that include the exposed surface of the substrate 111 in valleys formed between the masked regions 115. The substrate 111 can include silicon, germanium, Si—Ge, or other semiconductor materials. For example, the substrate 111 can include a p-type Si (100) wafer (e.g., boron-doped, 10-20 Ω·cm resistivity) with a thickness of 550 μm. One side of the exemplary p-type Si wafer can be mirror-polished. Before implementation of the process 110, the exemplary Si wafer can be thoroughly cleaned, e.g., following a RCA procedure (e.g., organic clean, oxide strip, ionic clean). In some examples, the process 110 can be implemented using lithographic techniques, e.g., including photolithography, deep UV lithography (DUVL), extreme UV lithography (EUVL), or nanoimprinting lithography (NIL). In one example, a line patterned mold of the masking material 112 can be formed on the silicon substrate 111 to create the pattern mask by spin coating a photoresist material (e.g., such as poly(methyl methacrylate) (PMMA) or SU-8) of the silicon substrate 111 and exposing the UV light exposure through a photomask and developing the pattern mask. In another example, a nanoimprinting or microimprinting technique can be utilized to press on the thermoplastic PMMA type resist under optimal temperature and pressure. After transferring the mold patterns, the remaining PMMA resist pressed by the protruded mold pattern can be removed through an oxygen reactive ion etching (RIE) process, e.g., because the PMMA resist prohibits silicon etching by not allowing physical contact with the silicon substrate.

The exemplary Si wafer can be cut into 20 mm×20 mm areas to serve as the substrate 111 to conveniently implement the method. For example, the substrate 111 can be configured from a 550 μm-thick Si plate wafer, or in some examples from a ~1,000 μm-thick wafer or 1 cm-thick Si block, which can be cut into 2 cm×2 cm areas to pattern a line array, for example, which can be configured with a width of 10-20 μm and a spacing of 20 μm, or in other examples, a narrower pattern of 5 μm wide×10 μm spacing can be implemented. The exemplary 5 μm width×10 μm spacing micropattern can be equivalent to having ~1,330 parallel lines, which means ~1,330 slices of 5 μm wide Si slices obtained simultaneously per cut.

The process 120 is performed to deposit an etcher layer 123, a magnetic guide layer 124, and a protection layer 125 on the patterned substrate 121 to form a composite etching structure 127. For example, the deposition can be conducted using sputtering, evaporation, ion beam, pulsed laser, or other deposition techniques. The etcher layer 123 can be formed of a first catalyst material, which is deposited on the surface of the patterned substrate 121. The magnetic guide layer 124 can be formed of a magnetic material on the etcher layer 123. The protection layer 125 can be formed of a second catalyst material on the guide layer 124. For example, in some implementations, the first and second catalyst materials can be the same catalyst material while in other implementations they may be different. The catalyst material can include a metallic catalyst material, e.g., including, but not limited to, gold, silver, palladium, or platinum. The magnetic material can include a ferromagnetic material, e.g., including, but not limited to, iron, cobalt, nickel, or their alloys. The composite etching structure 127 is deposited above the surface of the masked regions 115 of the masking material 112 and deposited above the surface of the substrate 111 in the unmasked regions 116. For example, in some implementations, a catalytic/ferromagnetic/catalytic trilayer thin film (e.g., Au/Fe/Au triple layer, with a thickness of 10 nm, 15 nm, and 10 nm, respectively) can be deposited by sputtering or thermal evaporation on the exemplary line patterned silicon substrate 121.

The process 130 is performed to apply an etching solution over the patterned substrate 121 that chemically reacts with exposed regions of the etcher layer 123 of the composite etching structure 127 and etches material from the substrate 111 at exposed surface of the unmasked regions 116 forming an etched or sliced region 136 inside the substrate 111. Notably, a magnet 139 is provided to apply a magnetic field to steer the composite etching structure 127 during etching. The steering can be controlled by controlling the direction and intensity of the applied magnetic field to provide an attractive force on the magnetic guide layer 124 to drive the composite etching structure 127 into the substrate 111. The chemical etching solution can include a hydrofluoric acid (HF) solution including HF, hydrogen peroxide ($H_2O_2$), and $H_2O$, in which $H_2O_2$ can function as oxidizing agent and HF to dissolve oxide. For example, when catalytic metal particles of the first catalytic material of the etcher layer 123 are in contact with the silicon substrate 111 and in contact with the chemical etchant solution, etching can begin at the contact interface between catalytic metal particles and the substrate. The catalytic metal particles of the etcher layer 123 penetrate into the substrate material (e.g., silicon) over time forming pores in the substrate 111, e.g., in which the etcher layer 123 reacts with the chemical etchant such as the exemplary HF solution to induce etching. The applied magnetic field generated by the magnet 139 produces a magnetostatic attractive force on the magnetic guide layer 124 (e.g., located in the middle of the composite etching structure 127) to steer or guide the directional movement of the composite etching structure 127 into the substrate 111, e.g., by accelerating a descending speed of the catalyst material to the surface of the substrate material. In some examples, the steering can be directed vertically for sufficient pore formation of vertically aligned nanowires of the exemplary silicon material, or in other examples, other shaped structured based on other directions of the steering of the composite etching structure 127. For example, the composite etching structure 127 can be configured as an array of straight lines or can be an array of curved lines, e.g., in which the curved lines configuration results in parallel sliced Si microsheets that are not flat sheets but are curved or undulating sheets.

Figure 1B:
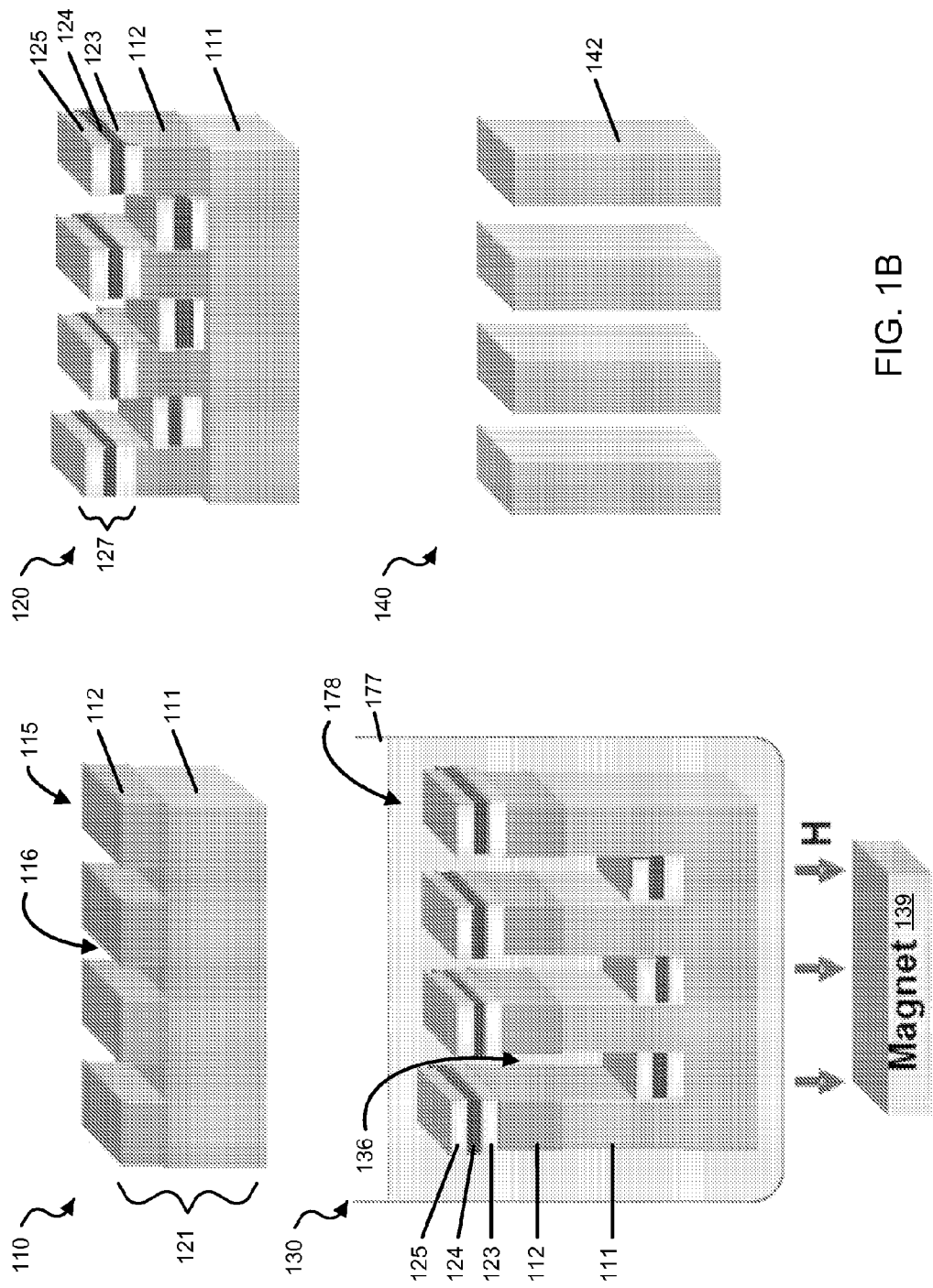
FIG. 1B shows a schematic illustration of an exemplary magnetically direction-guided slicing process.

In some implementations of the process 130, the composite etching layered patterned substrate can be placed into a container 177 containing an etchant solution 178, as shown in the schematic illustration of the exemplary magnetically guided electroless etching method in FIG. 1B. For example, the etchant solution 178 can be a mixture etchant solution of, for example, hydrofluoric acid and hydrogen peroxide with water, e.g., in which the $HF/H_2O_2/H_2O$ etching solution includes a volumetric ratio of 5:45:15, respectively. Various other aqueous etchant solutions containing a mixture of hydrofluoric acid and nitric acid ($HF+HNO_3$) or of hydrofluoric acid and ammonium fluoride ($HF+NH_4F$), or an $NH_4F$ solution can also be utilized for the magnetically guided Si etching process 130, e.g., with varying amount of $H_2O_2$ and $H_2O$ added to the solution. In the exemplary case of hydrofluoric acid and hydrogen peroxide mixture solution ($HF+H_2O_2$) type etchant, the concentration of HF can be configured in the range of 1-40%, and in some examples in the range of 5-20% by volume. The exemplary $HF+H_2O_2$ type etchant may also contain other chemical components such as NaOH, KOH, NH₄F, e.g., which can be configured less than 50%, and in some examples less than 10% by volume. Alternatively, for example, NH₄F solution in a water based solution containing $H_2O_2$ at a concentration of 10-50% may also be used.

For example, in some implementations of the process 130, the magnet 139 can be a permanent magnet (e.g., a Nd—Fe—B magnet with a strength of ~35 MGOe energy product and a dimension of 2 cm×4 cm×1 cm height) configured outside and underneath of a Teflon beaker, e.g., which can serve as the container 177, to supply a directionally (e.g., vertically) attractive force based on the magnetic field emanating from the exemplary Nd—Fe—B magnet 139 that pulls the magnetic guide layer 124 (e.g., which can include ferromagnetic Fe material sandwiched and protected between two Au catalyst layers 123 and 125 to form the composite etching structure 127).

The geometry of the etched or sliced regions 136 into the substrate 111 can be controlled based on the direction of the applied magnetic field. The depth of the etched or sliced regions 136 into the substrate 111 can be controlled based on the duration of etching and/or the etchant concentration and temperature. For example, shorter durations of etching of the patterned substrate 121 can result in sliced shapes in the substrate 111 to form a sliced material 141. For example, longer durations of etching (e.g., ~12-16 hours etching) of the patterned substrate 121 (e.g., such as the exemplary silicon wafer of ~250-550 μm thickness) can result in complete slicing through the substrate 111 to form separated sliced materials 142, as shown in FIG. 1B.

The process 140 is performed to remove the etched material from the etched or sliced regions 136 and any remaining composite etching structures 127 and masking material 112 from the sliced material 141. For example, acetone and etchant can be used to remove the remaining PMMA resists and the remnant three layers 123, 124, and 125, and the sliced material 141 can be washed thoroughly using deionized water. Cross-sectional and top-surface images of the sliced material can be verified using scanning electron microscope.

For example, without guidance of the magnetic layer, the etching process produces irregular nanostructures or nanopores in the substrate, rather than the desired slices. Also, for example, without guidance of the magnetic layer, the etching speed can be relatively slow, and the direction of the chemical etching can deviate from a desired vertical direction. For example, implementation of the magnetically guided electroless etching method can enable a kind of plane etching without forming silicon nanowires because the physical contact of the composite etching structure 127 with the exemplary silicon substrate 111 can be maximized during initial etching.

Figure 2:
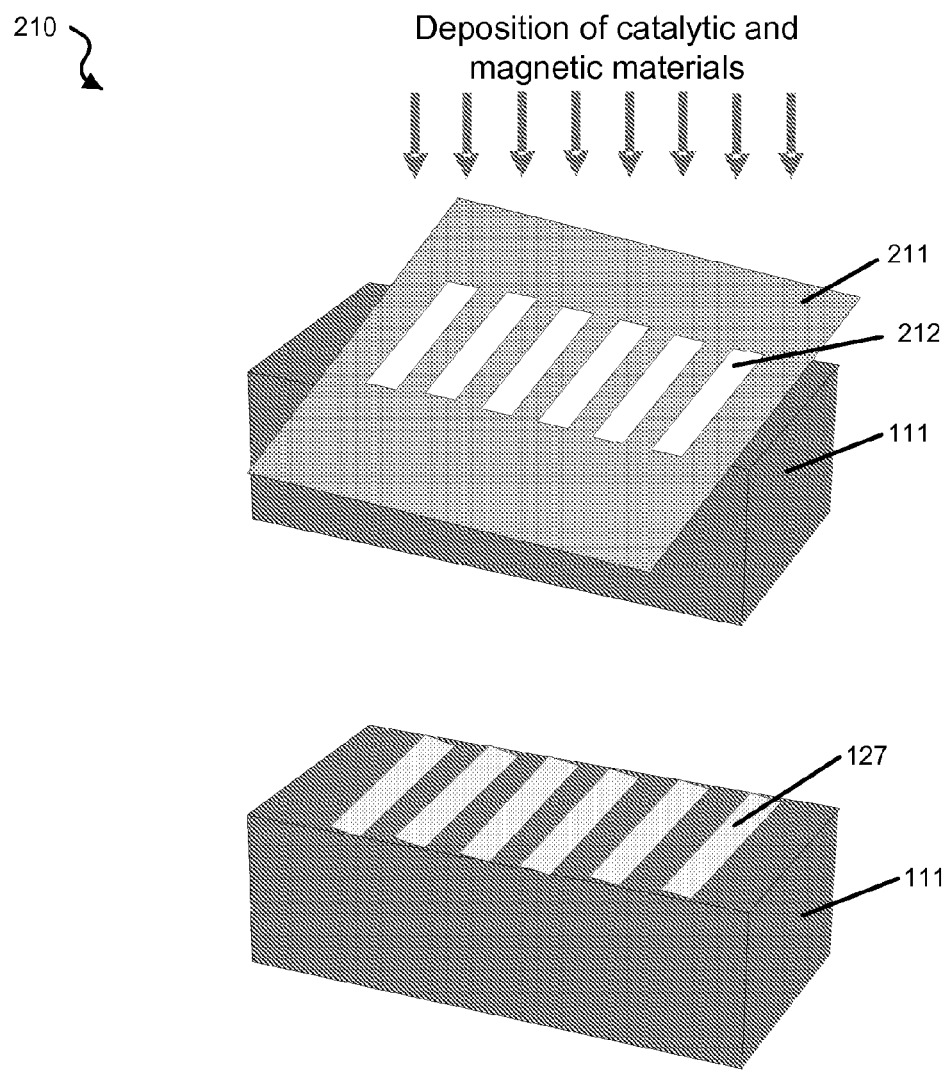
FIG. 2 shows a schematic illustration of an exemplary shadow mask technique.

FIG. 2 shows a schematic illustration of a method to implement the processes 110 and 120 using a shadow mask technique to pattern the composite etching structure 127 on the substrate 111, e.g., without implementing lithographic or nano/micro-imprinting processes in the magnetically guided electroless slicing method. The shadow mask technique can include a process 210 to place a shadow mask 211 containing slots 212 (e.g., including line slots, as shown in this exemplary implementation, or slots of other geometries or irregular patterns) over the substrate 111 to implement sputtering, evaporation, ion beam, pulsed laser, or other deposition techniques of the composite etching structure 127 to form the pattern for slicing the substrate material. Implementation of the process 210 can substitute for implementation of the processes 110 and 120 to perform the magnetically guided electroless slicing method.

The exemplary process 210 of the magnetically guided electroless slicing method also offers a convenient technique for slicing of round ingots by utilizing a curved shadow mask that conforms to the round geometry of the round ingots. For example, the shadow mask 211 can be made of metal foil such as Ni, Co, stainless steel or other metallic foils which can be either elastically bent or pre-bent to fit the round rod shape ingot surface curvature. For example, the shadow mask 211 can be made with a curved metal foil containing parallel line shaped slots through which the exemplary magnetic metal/noble metal materials of the composite etching structure 127 can be deposited on the ingot surface, e.g., including a zebra stripes shaped pattern, for subsequent etching/slicing. The shadow mask 211 can also be used in the process 110 as well, for example, to deposit photoresist material by rotating spin-coat or spray coat for selective PMMA resist layer on the ingot surface as a mask, or can be utilized for selective exposure, e.g., by UV exposure to form a stripe pattern on the PMMA precoated Si ingot surface. The catalyst metal/magnetic metal material triple layer can then be deposited to the recessed valley locations between the neighboring resist stripes. In one example of a curved pattern, a shadow mask geometry can include a 'zebra' pattern for the slots 212 on a curved stainless steel mask structure having a radius of curvature of 6 inches, e.g., with 50,000 slots of 10 μm width and 20 μm spacing, which can produce 20 μm-thick wafer slices by the guided etching method, or in other examples, 20 μm width and 50 μm spacing to produce 50 μm-thick wafer slices. For example, implementations of such a shadow mask approach can enable a rapid, high throughput manufacturing process.

Since no costly wire saw cutting machinery is needed, the slicing time is significantly and proportionally reduced by adjusting various process parameters, e.g., including the use of many simultaneous multiple bath containers 177 containing the substrates 111 to be sliced. For example, an arrangement of the multiple bath containers can include an array of 32×32=1,024 baths in a room. The exemplary process parameters can also include higher operating temperature of the bath, magnetic field gradient pulling strength, the amount of catalytic and magnetic material utilized, among other parameters, to further increase the slicing speed.

Figure 3A:
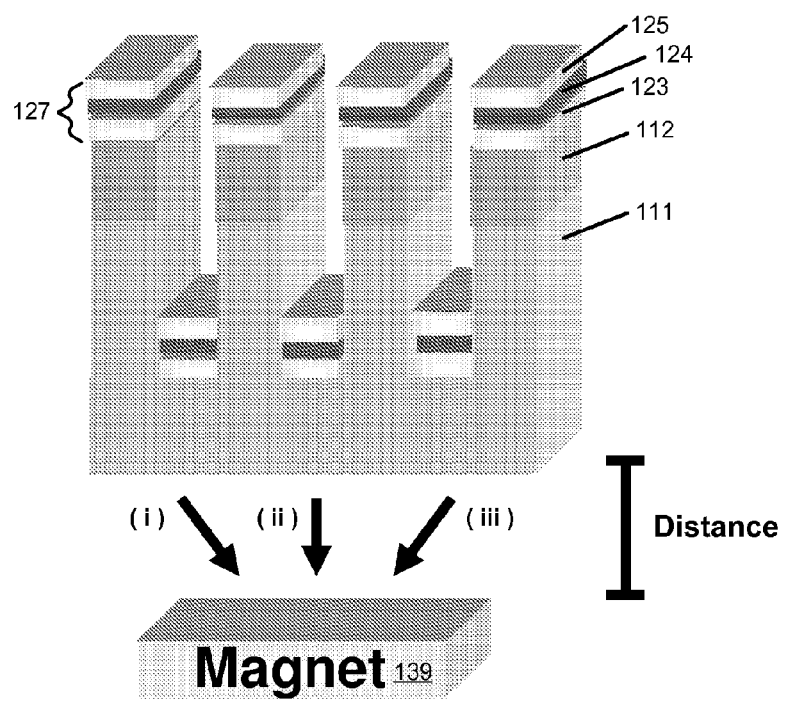
FIGS. 3A-3D show a schematic illustration and scanning electron microscopy (SEM) images showing variation of magnetic field directions on the exemplary magnetically guided electroless etching process.
Figure 3B:
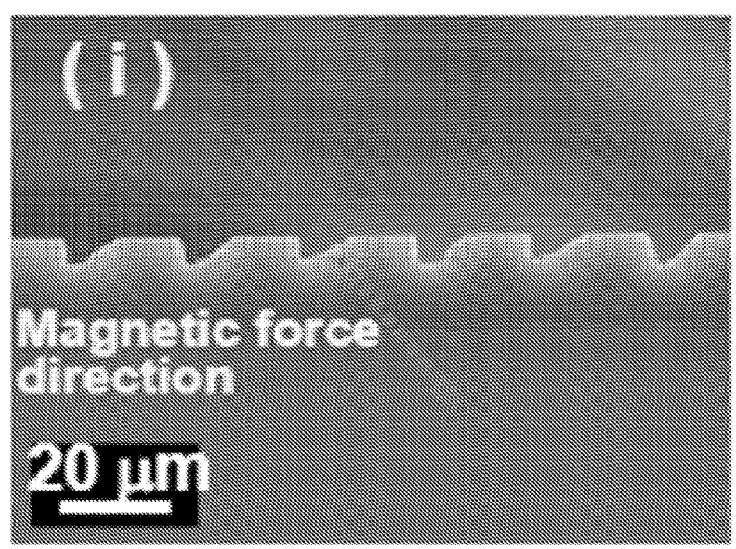
Figure 3C:
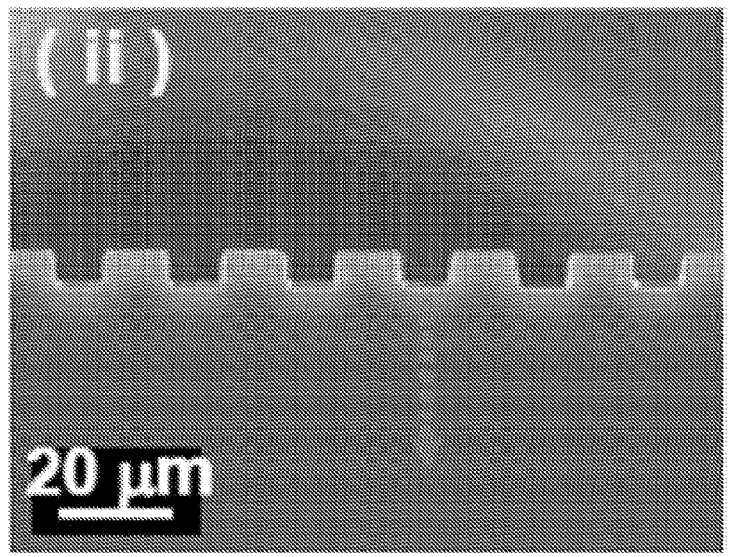
Figure 3D:
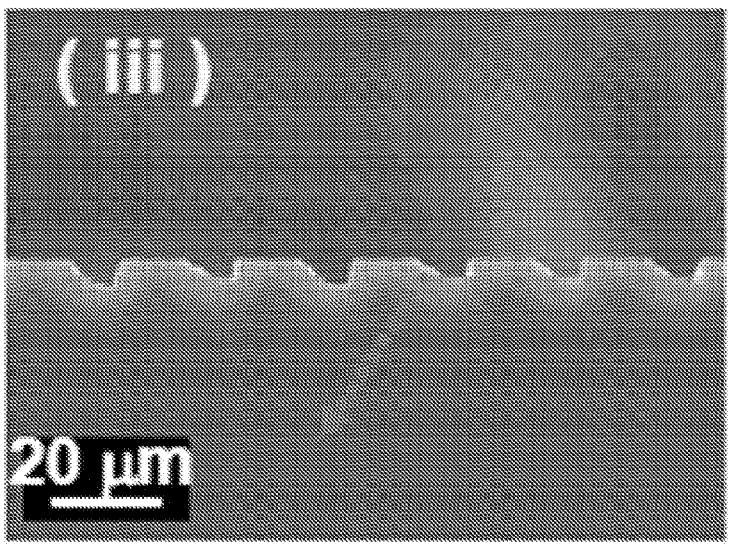

The disclosed magnetic slicing technique provides the ability to perform Si slicing at any desired directions by altering the magnetic field direction, e.g., which can ignore the crystallographic orientations of the substrate. FIGS. 3A-3D show a schematic illustration and scanning electron microscopy (SEM) images showing variation of magnetic field directions on the magnetically guided electroless etching process. FIG. 3A shows a schematic illustration showing variation of magnetic field directions from the magnet 139, e.g., which can be used to provide a relatively moderate 800 Oe magnetic field. The variation of magnetic field directions from a small magnet used in this experiment introduces different field directions to the exemplary Si substrate 111 being etched, which causes the chemical etching to be guided along the different orientations as indicated by the arrows in the FIGS. 3A-3D. FIGS. 3B-3D show SEM micrographs of the resultant altered Si slicing directions at an initial stage of the magnetically guided etching process 130 (e.g., for 10 minutes of etching using different magnetic positions), e.g., demonstrate that the silicon etching direction is affected by the magnetic force direction. As shown in the figures, the size, shape and placement of the permanent magnet in are such that the magnetic field is vertical in the middle part of the Si sample (FIG. 3C), while the field is tilted near the edge of the sample (FIGS. 3B and 3D). Due to the changes in magnetic force direction, the direction of silicon etching reveals a distinct change to the left side (FIG. 3B) and right side (FIG. 3D), as well as on the vertical direction in the middle (FIG. 3C).

For example, the ability to slice and prepare Si wafers cut along any crystal orientations can be useful for various Si electronics and other devices. Different Si orientations and non-(100) orientations provide different electronic and other physical characteristics, which can be useful for a variety of technical applications.

Exemplary implementations of the disclosed magnetically guided slicing method were performed to produce shaped and sliced silicon materials.

Figure 4A:
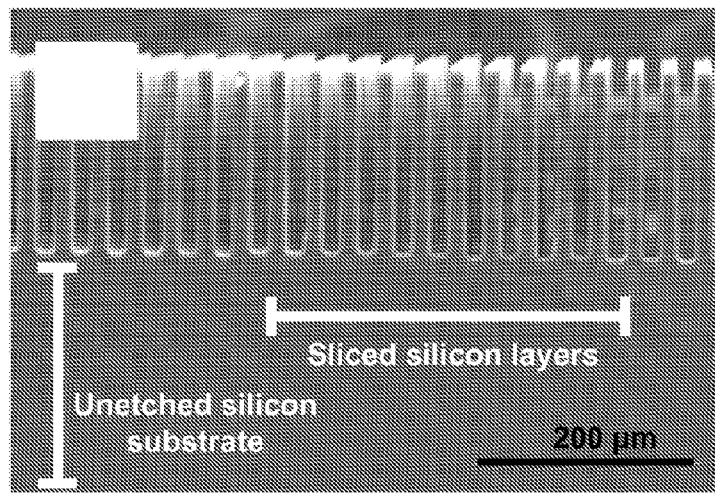
FIGS. 4A-4C show SEM micrographs of magnetically guided Si slicing to produce vertical microsheet arrays.
Figure 4B:
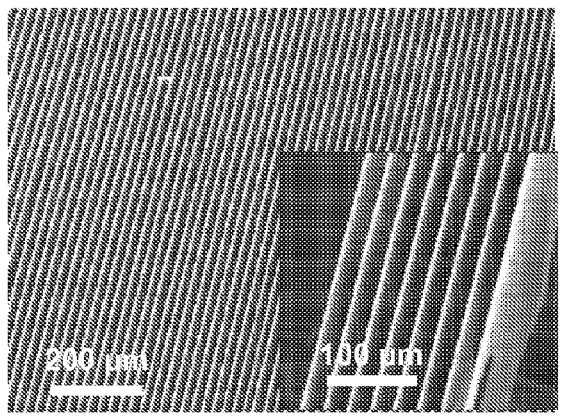
Figure 4C:
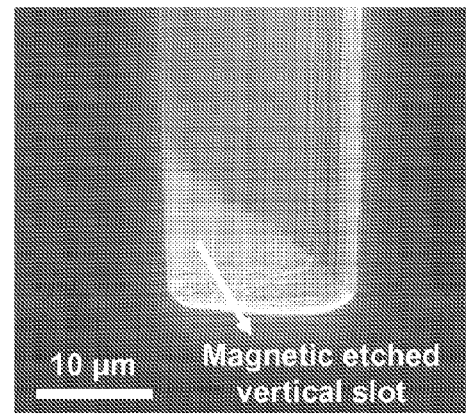

FIGS. 4A-4C show SEM micrographs of magnetically guided Si slicing to produce vertical microsheet arrays. For example, the SEM micrographs of FIGS. 4A and 4B show the vertical microsheet arrays with a ~10-20 μm thickness. The inset image in FIG. 4B shows a higher magnification image of the exemplary sliced Si microarray structure. For example, the Si substrate can be sliced in a through-cut manner or only partially sliced as a parallel array of microsheets attached to the remaining Si substrate. FIG. 4C shows a magnified image of the etched valley.

For example, the loss of Si material by slicing is very small using the disclosed method, e.g., as compared to the typical ~200 μm Kerf loss in wire saw cutting processes. In the example case shown in FIG. 4C, the loss was ~15 μm width per cut. The quality of sliced Si surface was relatively smooth but with nanoscale surface roughness. On a much higher magnification scale, the surface area of the side wall of a several micrometer thick sliced Si thin plate measured by Atomic Force Microscopy (AFM) for a 5 μm×5 μm area, e.g., using Veeco AFM model Dimension 3100, indicated that the average surface roughness ($R_a$) of the sliced Si surface was estimated to be ~8 nm, which is microscopically smooth but still absorbs more light than the typical Si surface. For example, a slight surface roughness on a solar cell surface can help to retain light with reduced reflectance of sunlight. A further intentionally-roughened surface of active photovoltaic Si surface can be obtained by implementing the described methods, which may optionally be used to reduce sunlight reflection for capturing and utilizing as much sunlight energy as possible.

Figure 5A:
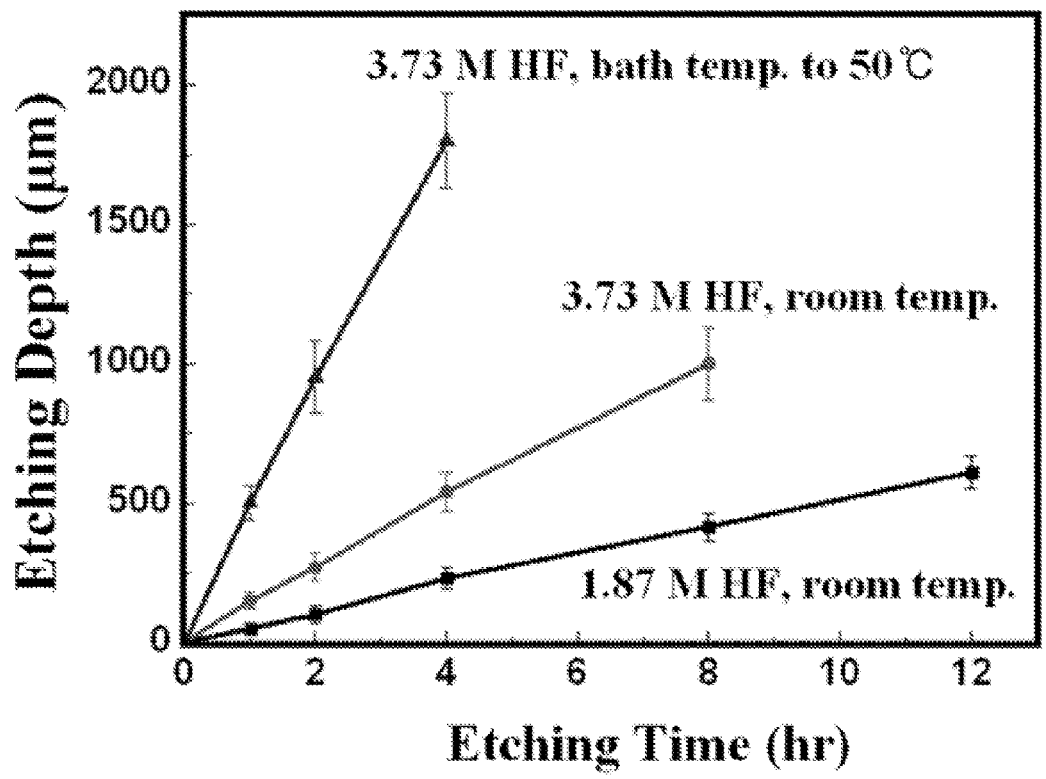
FIG. 5A shows a data plot demonstrating the magnetically guided Si slicing etch rate altered by acid concentration and temperature.
Figure 5B:
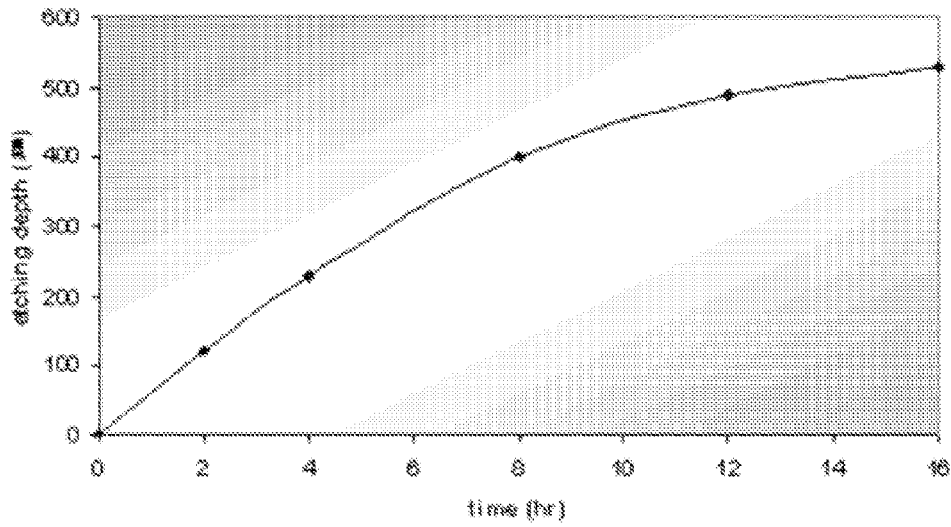
FIG. 5B shows a data plot demonstrating the depth of the silicon slicing based on the etching period.

The depth of catalytic Si slicing can be dependent on the etching time, the concentration of the etching solution, and the temperature of the etching solution bath, as exhibited in FIGS. 5A and 5B. FIG. 5A shows a data plot demonstrating the magnetically guided Si slicing etch rate altered by acid concentration and temperature. For example, as shown in the plot, the etch rate increased from ~50 μm/hr for HF solution (1.87 M) at approximately room temperature (18° C.) to ~120 μm/hr for HF solution (3.73 M) at the same room temperature, and to ~500 μm/hr for HF solution (3.73 M) at an elevated etching solution bath temperature of 50° C. The Si slicing was conducted in a massively parallel manner. In these exemplary implementations, the etchant composition included a mixture chemical etchant with a volumetric ratio of $HF:H_2O_2:H_2O=5:45:15$. For example, doubling of the HF concentration from 1.87 M (e.g., equivalent to ~7.7 volume % in $H_2O$) to 3.73 M together with the bath temperature raised to 50° C. increased the etch rate (slicing rate) by a factor of ~×10 to the etching speed of ~500 μm/hr. This exemplary data provides further indication that increase of etch rate can be optimized based on the etching solution and catalyst selection. For example, a periodic replenishing of etching solution or active stirring also substantially increases the slicing speed. The slicing speed is also dependent on the magnitude of the applied magnetic field since the magnetic attractive force exerts a vertical pull-down force on the exemplary Au/Fe/Au triple layer that causes the catalytic Si etching. It was observed that an increase of average applied magnetic field can increase the etch rate (slicing speed) by a factor of 2~3. The practical etching speed obtainable using the exemplary materials and parameters presented in this exemplary implementation is estimated to be at least 1,000-2,000 μm/hr.

FIG. 5B shows a data plot demonstrating the depth of the silicon slicing based on the etching period. The plot demonstrates that for the given triple layer geometry of the exemplary composite etching structure, the etching speed slows down somewhat as time passes. For example, after 16 hours, silicon gets sliced completely and at this time the thickness of the final sliced plates is about 10 μm each.

The Si slicing thickness can easily be changed by altering the triple layer line width and spacing. The etching time can also be changed to control the degree of etching, either for formation of deep grooves or for complete slicing. The magnetic attractive force can also be altered to influence the etch speed. The magnetic field orientation can be altered to produce Si slices or grooves with different crystallographic orientation of Si, Ge or their alloys.

The exemplary implementations included removing the remaining polymer resists by simple rinsing using acetone after the slicing is completed. For example, a common gold etchant solution was employed to remove any trace of the remnant composite etching structure (e.g., the triple-stack Au/Fe/Au layers). The exemplary completely-sliced silicon 142 can then be washed with deionized water. Optical intensity measurements from the sliced Si surface were performed with a ZEISS AXIO observer spectrophotometer.

For example, such convenient Si slicing with minimal loss of Si material can have significant implications, as the drastically reduced cost for single crystalline (or polycrystalline) Si wafer would make the crystalline Si photovoltaics much more cost competitive as compared to other renewable or fossil fuel energy sources. For example, the disclosed technology can produce as little as ~5-20 μm thickness of Si wasted per each wafer cut, e.g., as compared to the current wire saw cut with 0.200 μm cutting loss thickness. Furthermore, the ability for massively parallel cutting to produce thin Si wafers as thin as 5-20 μm offers an additional significant advantage of using thinner wafers for even lower cost photovoltaic solar cells. Also for example, another important aspect to consider includes the Si feedstock materials availability issue in that the overall Si materials consumption in photovoltaic solar cell industry, as well as in the semiconductor electronic device industry, which can also be reduced significantly by a factor of 10 to 20 if such thin-wafer-based solar cells and semiconductor devices that include silicon material made using the disclosed magnetically guided slicing technology can be made widely utilized.

In some implementations, etching of Si materials using particles such as Au, Pt, Pd, or Ag can be employed. In Equation 1 describes the etching process that begins by reducing $H_2O_2$. Generally, the silicon etching process can be slow due to the low catalytic capability of silicon in an $HF/H_2O_2$ solution.

$$H_2O_2 + 2H^+ = 2H_2O + 2h^+ \qquad (1)$$

The exemplary metals such as Au, Pt, Pd, or Ag can be used as a catalyst to produce positive holes in silicon as it donates electrons to $H_2O_2$ and takes in electrons from the silicon. As shown in Equation 2, the positive holes produced make oxidative dissolution of silicon in solutions that include HF. Since this mechanism occurs on the interface contacting with metals, etching process is conducted continuously in the surface in contact with metal.

$$Si + 4h^+ + 6HF = SiF_6^{2-} + 6H^+ \qquad (2)$$

The exemplary Au/Fe/Au trilayer configuration of the composite etching structure can be utilized for the following advantages. For example, with the presence of magnetic attraction below the silicon, the Fe layer in the middle of the composite etching structure can prevent Au films from peeling off easily on the silicon substrate, which can happen in initial etching, and the occurrence of silicon nanowires can be reduced by inducing consistent physical contact with the Au films and the silicon. Also, for example, the magnetic layer such as Fe, Co, Ni and their alloys can enable magnetically direction-guided chemical etching, along the exact vertical direction for the straightforward slicing purpose, or at an angle for other device applications that utilize tilted slicing or groove formation for devices needing different Si crystal orientations. The applied magnetic field can accurately guide the direction of the vertical slicing without undesirable, off-axis slicing. The magnetostatic attractive force on the ferromagnetic layer can also accelerate the descending speed of the catalyst lines for more rapid slicing speed.

On continuous chemical etching, the Fe film may become slowly dissolved and disappear if the HF solution is used for an extended amount of time, as in some of the exemplary conditions. In such exemplary cases, this phenomenon produces the dramatic effect that enables silicon etchings to happen twice as the Au film, which naturally exists on the upper part, moves down again to the same position. For example, while gold is essentially insoluble in hydrophobic acid, gold may be slightly etched in a certain combination of acids. For example, the silicon structures that cannot be etched during the first trial with etcher layer (e.g., the lower catalytic material) can be etched during a second trial with the protective layer (e.g., the upper catalytic material) as the protective layer comes down into the valley, in which the protective layer etches again the remaining non-etched silicon structures to induces a clean plane etching. For example, a multilayered composite etching structure (e.g., (Au/Fe/Au)n, where n=1 to 20) can be utilized for more powerful magnetic guiding and for further accelerated etching/slicing speed due to the increased magnetic material. The multilayer configuration also makes the Si etching/slicing continue for longer time and thickness.

For example, for silicon etching guided by magnetic force using the described techniques, the etching speed accelerates relatively upon physical contact with the silicon as induced by the strong magnetic influence in the early stage of the etching. For example, after a few hours, however, the magnetic force influence can diminish somewhat as the magnet layer can eventually be dissolved by the HF solution. In this example, the etching process slows down because only the etching process between the catalyst film and silicon remains without the contribution of attractive magnetic force. Thus, the use of a thicker magnetic layer or etcher layer, as well as the use of a multilayered composite etcher structure, e.g., such as a (Au/Fe/Au)n configuration, or use of an envelope-protected magnetic layer, or use of more corrosion-resistant magnetic layer such as CoPt or FePt, can prolong the effective magnetically-guided etching process.

While the speed of directionally-guided Si etching may seem slower, this type of slicing can be conducted with many thousands of parallel triple lines and on many Si blocks simultaneously in a single etching bath. For example, on a 12 inch Si block, there can be 30,000 parallel lines of 5 micrometer wide triple layer lines at a 5 micrometer spacing placed for simultaneous etching. Furthermore, 10-1000 wafers can be etched at the same time in a large chemical etch bath, and many hundreds of Teflon baths can be operated simultaneously for parallel batch processing. Thus, the average etching time for each slice can be very short.

In the absence of the magnetic layer in the exemplary Si etchline array, the slicing of Si can result in a random, uncontrolled nanowire geometry, as compared to the desired microsheet configuration. FIGS. 6A and 6B show SEM micrographs depicting the Si etching using 5 nm and 10 nm thick Au thin film lines, respectively, in the absence of the magnetic layer (of the composite etching structure) and under exemplary conditions including 4 hr slicing time under etchant conditions of 0.87 M HF in $H_2O$ at room temperature. As shown in FIGS. 6A and 6B, it is evident that the resultant etched Si has an undesirable, random nanowire geometry. FIG. 6C show SEM micrographs depicting the results of silicon slicing by the composite etching structure but without the applied magnetic field and under similar under exemplary conditions, e.g., but with 2 hr slicing time. In this exemplary case, the results show some crooked and non-uniform etching, e.g., most likely due to the existence of three different variations of the easily etchable <100> orientations along the x, y, and z directions. FIGS. 6D and 6E show SEM micrographs depicting the Si slicing process utilizing the magnetic composite etching structure with the applied magnetic field, e.g., for a 40 minute slicing time (FIG. 6D) and a 3 hr slicing time. It is noted that in these exemplary implementations using the magnetic composite etching structure with the applied magnetic field, the shaped and sliced materials exhibited a periodic, well defined slices in the microsheets.

The disclosed slicing techniques can also be useful for dicing small semiconductor devices or a small group device aggregates from a large-scale Si or Ge wafer containing many simultaneously manufactured electronic, optical, magnetic, MEMS or memory device arrays. For example, the disclosed parallel dicing techniques using the magnetically-guided etching can be much more efficient, faster and cheaper than the mechanical saw cutting or laser cutting. Also, for example, the disclosed magnetically guided Si slicing techniques can be useful for creating nonconventional Si geometries, which can lead to broader scientific innovations, new device phenomena, and new technological applications.

Exemplary flexible Si-based devices fabricated using the disclosed magnetically guided electroless etching technology are described. For example, since the magnetically guided slicing technique can produce very thin Si wafers as thin as ~5 μm (and even thinner), flexible or conformable Si devices and circuits can be constructed from such thin Si wafers fabricated by the disclosed techniques. For example, there are many exciting potential applications using thin Si, including, but not limited to flexible displays, sensors, actuators, integration of compliant semiconductor chips for in vivo biomedical applications on curved surface. Furthermore, since the magnetic field guides the direction of Si slicing in the disclosed techniques, off-axis orientation Si wafers (e.g., non-(100), (110), (111) Si wafers) can be created by the disclosed technology. Such different crystallographic orientations of Si wafers may lead to interesting and new semiconducting, photonic, optoelectronic, and mechanical properties which might be exploited to create new devices with exciting characteristics.

For example, micro tunnel formation within a Si crystal can be produced by implementations of the disclosed technology. FIGS. 7A-7F shows SEM images and schematic illustrations of nonconventional geometries of silicon materials fabricated by implementing the disclosed techniques.

The magnetically guided Si etching technique can also be utilized for microscale tunneling for unique applications such as microfluidic channel devices, micro fuel cells, and micro combustion channels, among other applications. For example, such tunnels do not need to be straight tunnels as curved tunnels are sometimes desirable. Curved- or zig-zagged-shaped tunnels may also be drilled by gradually manipulating magnetic field directions by implementing the disclosed technology, as shown in FIGS. 7A-7C.

FIG. 7A shows an SEM micrograph of exemplary ferromagnetic bead microsphere with catalytic Au surface coat that can be implemented in the disclosed magnetically guided etching techniques. FIG. 7B shows a sectional SEM micrograph of a silicon material with a microscale curved tunnel drilling into the silicon using the disclosed magnetically guided etching techniques. FIG. 7C shows a schematic illustrating the principle of guided tunneling into a silicon material, e.g., silicon wafer 701. For example, microspheres 701 formed of the exemplary ferromagnetic bead cores with catalytic Au surface coatings (e.g., 1-2 µm in diameter) can be brought into contact (e.g., deposited) on the wafer 701. For example, the Au catalyst coating can be coated on ~1-2 µm diameter silica containing ~45 volume % magnetic nanoparticles of $Fe_3O_4$ (e.g., ~40 nm thick, which can be deposited by thiol conjugation attachment of Au nanoparticles and additional electroless Au plating). For example, the surface Au catalyst of the microspheres 702 reacts with the Si wafer 701 and catalytically etches it at the contact interface, e.g., as the Au-coated magnetic spheres are pulled by applied magnetic field force applied by a magnet 703 that is moved along an arc-like path, thus forming a micro-tunnel. An array of microtunnels can be made in parallel by appropriate positioning of the magnetic particles in advance.

FIG. 7D shows an SEM micrograph of an exemplary tall Si microwire array (~1 µm diameter and 100~200 µm tall) on large area Si surface, e.g., prepared by magnetically guided chemical etch directions. For example, the composite etching structure can be configured in a 'Swiss-cheese' configuration in which a trilayer of Au/Fe/Au (e.g., having 10 nm Au, 15 nm, and 10 nm Au dimensions) can include an array of holes, e.g., 20 µm in diameter. The exemplary Swiss-cheese composite etching structure can be magnetically pulled downwards using a permanent magnet, as shown in the process 130 in FIGS. 1A and 1B. In some implementations, the hole area may not be etched by the etching solution (e.g., $HF/H_2O_2/H_2O$ etchant), but the outside regions can continue to be etched downwards, thus creating an array of tall Si pillars, as shown in FIG. 7D. Tall Si micrometer arrays of a only a few micron diameter and the height in excess of 300 µm have been obtained, with a very high aspect ratio of ~50-100 or even greater using the exemplary Swiss-cheese configuration of the magnetic guided Si etching method.

FIG. 7E shows an SEM micrograph of exemplary bent Si nanowires (e.g., ~700 nm diameter) by the disclosed magnetic guided etching techniques. For example, by utilizing the exemplary Swiss-cheese patterned composite etching structure deposition, e.g., similar to the process 120, and by altering the magnetic field orientation at specific desired time and at certain desired etched lengths, e.g., similar to the process 130, an abruptly bent or gradually curved Si nanowire array can be obtained. An exemplary zigzag Si or nanowire array with a smaller diameter and of higher density can also be fabricated using the exemplary Swiss-cheese configuration of the magnetic guided Si etching method.

FIG. 7F shows an SEM micrograph of a dense forest of an exemplary array of zigzag Si nanowires (e.g., ~300 nm diameter) by ~30 degree direction-changing magnetic etching steps (e.g., with a total etch time of 2 min). For example, the exemplary implementation to produce the array of zigzag Si nanowires included applying a magnetic field with a magnetic field strength of ~800-1,000 Oe. The exemplary zigzag bending can be repeated many times by changing the magnetic field direction through repeated movement of a permanent magnet or by selective pole activation of a multi-pole electromagnet. For example, by controlling the lengthwise degree of chemical etching, the exemplary zigzag nanowires can also be made with a gradient diameter, with the diameter gradually increasing at the lower side. The exemplary zigzag nanowires of Si, Ge or Si—Ge, or other semiconductor materials, can be made into a variety of geometries with nanowire diameter regime of, e.g., 100 nm to 100 µm, and the height regime of, e.g., 1 µm to 10 cm, and the bent angle change of at least 1, and in some examples at least 3 along the length of the nanowire.

Figure 8A:
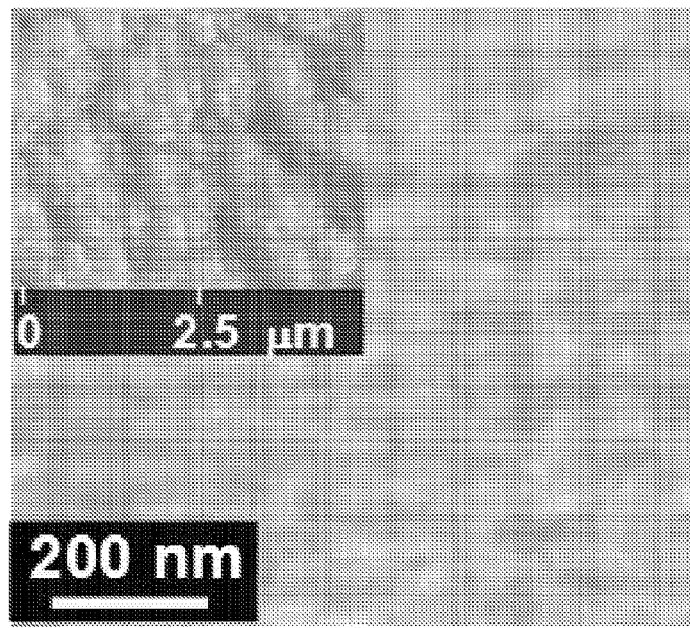
FIG. 8A shows an SEM micrograph and atomic force microscopy (AFM) data of the surface of an exemplary 10 μm-thick Si microsheet.
Figure 8B:
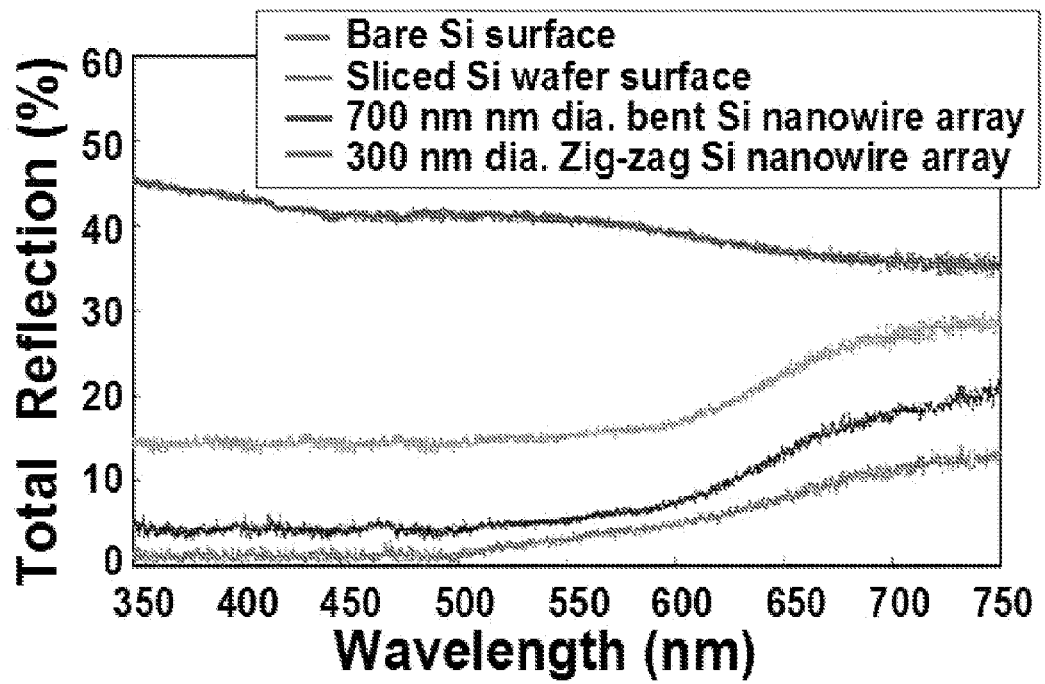
FIG. 8B shows a data plot of the light reflectivity of various Si surfaces and Si nanowire structures.

FIG. 8A shows an SEM micrograph demonstrating the relatively smooth surface of an exemplary 10 µm-thick Si microsheet slices by the magnetic Si slicing techniques. The inset image in FIG. 8A shows AFM data of the sample. FIG. 8B shows a data plot of the light reflectivity (e.g., % total reflection) of various Si surfaces and Si nanowire structures. The data plot shown in FIG. 8B shows a trend of reflectivity decrease by surface roughness caused by zigzag nanowires, e.g., albeit with unoptimized dimensions. It is notable that the as-sliced Si itself has a nanoscale surface roughness and much reduced reflectivity, as is often desired for solar cells.

For example, once the exemplary zigzag Si nanowire array is fabricated (e.g., on a substrate), it can be utilized as a template to prepare a host matrix template that enables to deposit any electroplateable metallic wires into zigzag nanowire shape. For example, a PDMS or PMMA type polymer can be cast on the zigzag Si nanowires, and Si nanowires are then etched away to leave a zigzag pore array into which metallic wires can be electroplated. The template of PMMA can then be dissolved away to leave metallic nanowire array. The metallic nanowires can be made from any electroplateable metals or alloys, e.g. including, but not limited to, Fe, Ni, Co, Cu, Ag, Au, Zn, Sn, Sb, Bi and their alloys. Synthesis of the exemplary zigzag nanowires can be useful for a variety of new nanotechnology-based applications. For example, the exemplary zigzag nanowires of Zn can be electrodeposited followed by controlled oxidation and annealing to form zigzag ZnO nanowire arrays that have useful properties of e.g., such as implementation of piezoelectric nanowires. For example, any metallic zigzag nanowires produced using the described synthesis method can also be coated with metallic, ceramic or carbon material by sputtering or electroplating to make core-shell zigzag nanowires. Also, for example, the core metal can also be etched away to produce a nanotube array in a zigzag configuration.

For example, as shown in FIG. 8B, the exemplary zigzag Si nanowires exhibit significantly improved anti-reflection (AR) coating properties. Efficient anti-reflection coatings can be essential for maximizing solar energy absorption with minimized reflection loss of sunlight. For example, the AR coatings can also be useful for various miniaturized optical sighting systems, enhanced light transmission and imaging, and reduced sunlight loss in solar cells and other energy devices as well as other civilian and military optical system lenses such as for glint-free, stealth movements/operations of soldiers. As the natural light and solar radiation are of broadband type, the AR coating needs to be effective over a relatively broad light spectrum. The AR coating also has to be effective for all angles of light incidence for many technical applications, as tilted or glazing angle incident light can cause much greater magnitude of light reflection.

Existing anti-reflection coatings such as the honeycomb-type anti-reflection device (ARD) suffer from the loss of transmission over broad fields-of-view, including the problem of "blue shift", which can cause a loss of critical spectral transmission and lead to unwanted reflections from the front lens or loss of spectral resolution. The disclosed zigzag structures can be used as an artificially modified surface structure that can increase the bandwidth. For example, the exemplary zigzag Si nanowires or zigzag $SiO_2$ nanowires (e.g., by oxidizing the Si nanowires) produced by the disclosed guided magnetic etching techniques are mechanically strong and adherent, e.g., since they are still part of the original substrate after etching and shaping. For example, the fabrication process of the exemplary zigzag Si nanowires or zigzag $SiO_2$ nanowires can be scaled-up to larger area substrates and optional multiple aqueous bath productions, e.g., without costly vacuum deposition equipment required in other techniques.

The catalyst material and configurations of the catalyst material can affect the described magnetically guided electroless etching technique and the articles fabricated through its implementation. For example, as the magnetic Si slicing speed and etching efficiency is influenced by the types of the catalyst utilized, it is important to properly select and control the catalyst materials and structures. Nobel metals, e.g., including, but not limited to Au, Ag, Pt and Pd, or their alloys between the noble metals, or alloys containing less than 10% of transition metals, can be utilized for the disclosed magnetically guided Si shaping and slicing techniques. Exemplary implementations of the disclosed techniques for Si etching demonstrated that an Au etcher layer functioned reliably among the exemplary noble metals. However, for example, it is noted that in the interest of accelerated Si slicing speed, the use of Pt as an alloying element to Au is beneficial. For example, a Pt layer catalyst line produced much faster Si etching during the magnetically guided slicing process than the Au layer catalyst line under similar process conditions. However, for example, it is noted that the exemplary Pt layer etched the Si material with somewhat more difficulty of etching control than the slower-etching Au catalyst layer. Thus, in some implementations, an Au catalyst etch line array is alloyed with Pt to provide both ease of etching control and faster kinetics. For example, according to the binary alloy phase diagram of the Au and Pt alloys, gold and platinum form a continuous solid solution in the Au-rich composition regimes and a two-phase mixture of terminal solid solutions. The desired composition of the Au—Pt alloy for the trilayer magnetic etchline containing magnetic layer can be in the range of 0.1-50% by weight, and in some examples 0.1-20% or even 0.1-10%.

The catalyst material and configurations of the catalyst material can affect the described magnetically guided electroless etching technique and the articles fabricated through its implementation. For example, the magnetic material that guides the Si slicing and shaping direction, and also accelerates the etching kinetics, is also an important parameter for consideration in selection and uses. In some implementations, the magnetic layer of the composite etching structure can include a chemical composition and magnetic properties of Fe, Ni, or Co or their alloys. For example, instead of pure iron, a Fe—Co alloy (e.g., Fe-35% Co alloy having ~20% higher magnetic saturation of ~24 KGauss) can be deposited and utilized for stronger magnetic pulling force in the Si slicing and etching. In some implementations, the composition of the magnetic layer can include Fe, Co or Ni, or an alloy comprising at least 50% by weight of Fe, Co or Ni or their combinations. Other elements in the periodic table, e.g., such as transition elements and common alloying elements such as Al, Mg, Ca, Ba, Sr, Si, Ge, and rare earth elements, can be present in the magnetic alloy layer in the combined amount of less than 20%, and in some examples, less than 50% by weight in the interest of magnetic properties. Also, for example, instead of soft magnetic Fe, Fe—Co, Fe—Ni, Co—Ni alloys, an intermetallic compound permanent magnet alloys of CoPt or FePt (L1o type structured phase) exhibiting high crystal anisotropy and high coercive force can also be utilized. These materials can be made into either magnetically hard alloy with a very high coercive force of Hc>~10 KOe or into a soft magnet alloy with coercive force of only a few hundred Oe based on the processing conditions and crystallization processes employed. The exemplary hard magnet alloy layers deposited on the Si surface to be sliced/shaped can optionally be pre-magnetized to the opposite polarity to that of the magnet facing the magnetic layer so that the external Nd—Fe—B magnet can pull the magnetic etchline arrays for accelerated slicing. Alternatively, for example, the CoPt or FePt or CoPd magnet alloy film etchlines can be magnetized to the same polarity as the magnet facing the etchlines (e.g., in the case of the magnet placed above the Si block to be sliced), so that the magnetic field from the magnet can help to push the catalyst etchline array downward into the Si (by magnetic repulsion of the same polarity magnetic materials) for enhanced Si etching.

FIGS. 9A-9E show schematics of various configurations of the exemplary composite etching structure. FIG. 9A shows a schematic of a configuration of a composite etching structure 900 including an Au/Fe/Au trilayer with a Au etcher layer 901, a Fe magnetic layer 202, and an Au protective layer 903. In other examples, the composite etching structure can include a Pt/Fe/Pt trilayer, an Au/CoPt/Au trilayer, a Ag/CoPt/Ag trilayer, or an Au/FePt/Au—Pt alloy trilayer.

FIG. 9B shows a schematic of a configuration of a composite etching structure 910 including an etching structure of a catalyst material 911 enveloping a magnetic material 912, e.g., in which the catalyst material 911 protects the magnetic alloy from getting dissolved, especially for prolonged magnetic guiding capability during long-period Si slicing operations. The magnetic pulling force is not affected much by such an enveloped arrangement. The catalyst material 911 can include, but is not limited to, Au, Ag, Pd, Pt or their alloys. The magnetic material 912 can include Fe, Co, CoPt, and FePt.

FIG. 9C shows a schematic of a configuration of a composite etching structure 920 including a magnetic layer 922 having a plurality of magnetic island structures 922a embedded in a catalyst material 921. For example, magnetic material, e.g., such as Fe, is precipitated in the form of islands embedded and protected by surrounding catalyst metal matrix, e.g., such as Au. Such an embedded configuration can prolong the useful lifetime duration of the magnetic material in the magnetic layer 922. For example, the Au—Fe binary alloy phase diagram indicates a mostly immiscible nature of the Au and Fe and the two-phase alloy regime of 30% Fe phase embedded in the ~70% volume Au phase. The composite etching structure 920 can be produced by thin film sputtering using co-sputtering method or alloy sputtering approach with a warm substrate temperature to form such two phased layer materials.

FIG. 9D shows a schematic of a configuration of a composite etching structure 930 including a magnetic layer 932 enveloped by protective enveloping layer 933, e.g., such as Teflon or other acid-resistant polymer layer, which is embedded in a catalyst material 931. For example, such a double protection can be constructed by step-by-step deposition process, which can be especially useful if there are pinholes in the Au layer in the deposited etchline array.

FIG. 9E shows a schematic of a configuration of a composite etching structure 940 including a porous magnetic layer of a magnetic material 942 that is configured between two porous layers of a catalyst material 941. For example, the porous catalyst material 941 can include, but is not limited to, Au, Pt, Pd, Ag, or their alloys. For example, the magnetic material 942 can include, but is not limited to, Fe, Co, FePt, CoPt, or CoPd. The porous catalyst material 941 and the magnetic layer 942 are intentionally made porous with nanopores having a dimension of 2-100 nm diameter, or in some examples 2-20 nm diameter, and a pore volume of at least 10%, and in some examples at least 30%. For example, such pores can be fabricated by oblique incident deposition, or by using a sacrificial metal islands incorporated into the thin film deposition which can then be chemically etched before or during the Si slicing etching operation. These added pores can facilitate the penetration and diffusion of the etchant to the interfacial Si surface that is facing the catalyst surface and is being chemically etched. Such enhanced diffusion can help to maintain the concentration gradient at the interface for more rapid Si etching and slicing.

FIG. 9F shows a schematic of a configuration of a composite etching structure 950 including a magnetic layer 952 and a porous layer of a catalyst material 951 forming a bilayer. For example, since both the catalyst layer and the magnetic layer are porous, an protective upper catalyst layer (e.g., of Au material) may not be needed, especially if CoPt type etching0-resistant magnetic layer is used. Also, for example, all of structures shown in FIGS. 9A-9F can optionally be repeated to form a multilayer structure or stacked structures, e.g., including structures 5-20 times stacked.

The magnetic field strength can affect the described magnetically guided electroless etching technique and the articles fabricated through its implementation.

For example, the changes in magnetic field strength vs. the distances between the catalyst layers and the magnet indicate that the magnetic field strength from the magnet is reduced as the distance from the magnet surface is increased. The distance between the Si wafer sample and a magnet can be configured to be about 10 mm in some exemplary implementations, e.g., as the etchant solution and silicon sample occupy certain volume within the exemplary container (e.g., such as a Teflon beaker). The permanent magnet can be placed below and outside the beaker.

Figure 10:
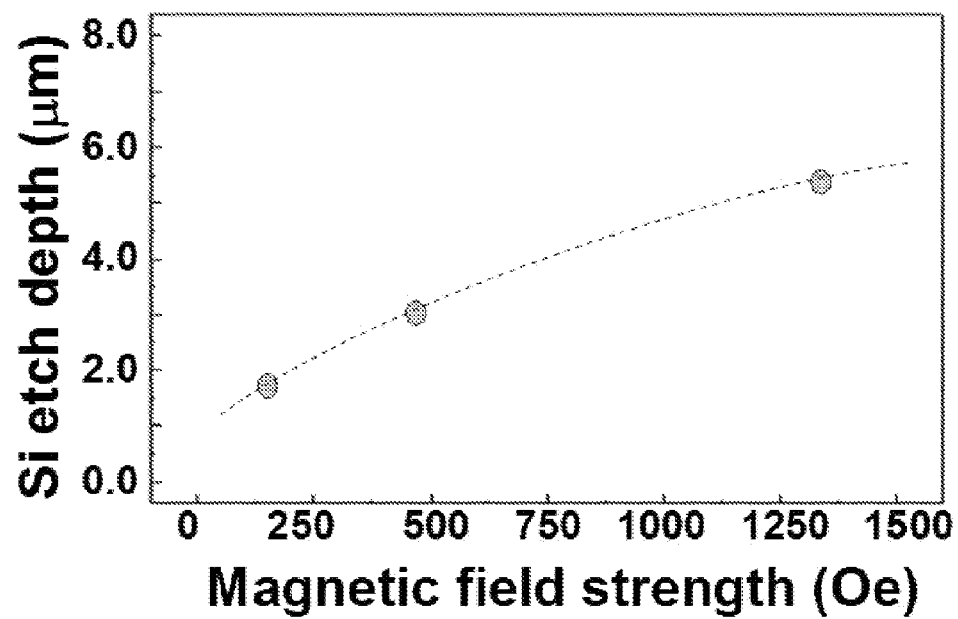
FIG. 10 shows a data plot showing the effect of applied magnetic field strength on the etching depth.

FIG. 10 shows a data plot showing the effect of applied magnetic field strength on the etching depth. The exemplary Nd—Fe—B permanent magnet was positioned at different distances to change the applied magnetic field strength. The data plot exhibits an increase of average applied magnetic field from ~200 Oe to 1,300 Oe increased the etch rate (slicing speed) by a factor of ~3. These exemplary magnetic field values are rather moderate fields that can easily be provided by inexpensive permanent magnets such as Nd—Fe—B. Also, for example, instead of a permanent magnet, an electromagnet can also be utilized for higher magnetic field and increased magnetic pull force.

For example, for Si ingot slicing to obtain wafers for solar cell or electronics use, the slicing speed is an important parameter that determines the throughput and processing cost of the wafer slicing. For example, the average slicing time for each wafer using the described guided catalytic chemical slicing techniques (e.g., that can exhibit speeds on the order of at least 1,000-2,000 μm/hr) can be estimated as follows. Since there is no complicated and costly equipment needed in the disclosed chemical slicing of Si ingots, many Teflon baths can be operated simultaneously on a plant floor. For example, if an array including 100 to 1,000 parallel slicing baths is utilized, e.g., with each bath having a 30 cm long (or longer) ingot with 15.6 cm×15.6 cm width and thickness dimension being sliced into ~4,000 wafers of 50 micrometer thickness with 20 micrometer Kerf loss per wafer slicing, then ~400,000 to 4 million wafers (for 100 to 1,000 parallel baths) can be sliced in ~7 days at a 1,000 μm/hr etch speed. This exemplary estimation results in a slicing time of less than ~2 to 0.2 seconds per wafer (for 100 to 1,000 parallel baths). Therefore a significant cost reduction can be achieved by using the exemplary magnetically guided, massively parallel Si slicing.

Figure 11:
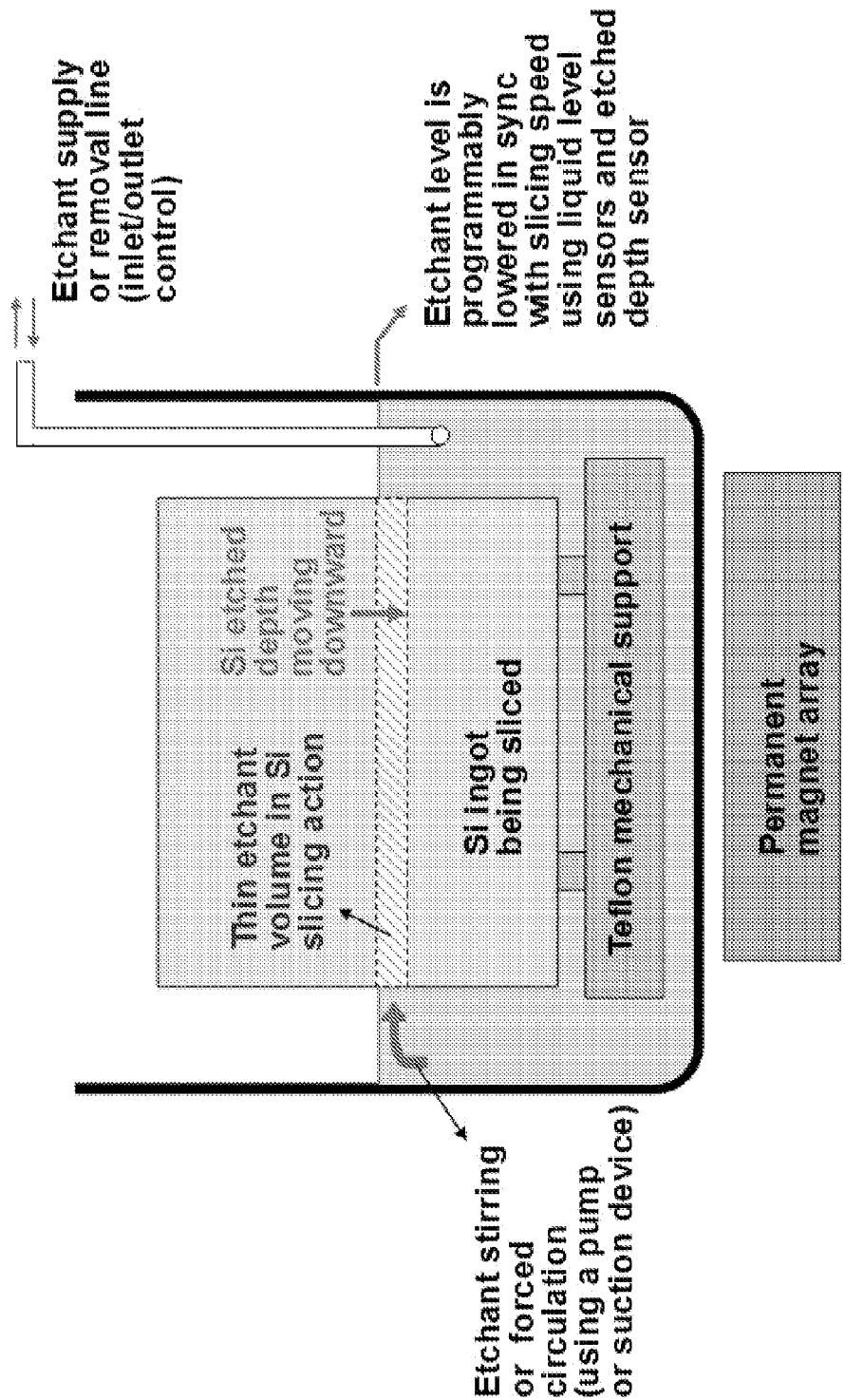
FIG. 11 shows a schematic illustrating a process to control the etchant height in synchronization with the slicing speed during the exemplary magnetically guided electroless etching process.

FIG. 11 shows a schematic illustrating a process to control the etchant height in synchronization with the slicing speed exemplary magnetically guided electroless etching process, e.g., of chemical slicing of a Si block. For example, the etchant height can be programmably adjusted so as to maintain a minimum amount of etchant just above the etched depth. For example, the process illustrated in FIG. 11 can be implemented in the event there are some chemical contaminants accumulating on the sliced Si wafer surface, such that the process ensures that the already-sliced Si portion is no longer exposed to the working etchant solution in the bath, e.g., by a time-synchronized lowering of the etchant level in such a way that the etchant height is controlled and limited only to the level slightly above the Si etched depth for continued etching/slicing. Various mechanical controls can be implemented in this process, e.g., including gradually lowering the etchant level, which can include mechanical pumping suction or positive-pressure pushing/supplying of fresh etchant solutions near the regions of active etching, microfluidic control of etchant supply.

For example, in some implementations, the etchant level can be configured to be at most 1 cm above the already-sliced valley height, e.g., at most 5 mm above the valley height, and in some examples at most 2 mm above the valley height. Such a localized and limited supply of etchant solution to the etched slot bottom regions minimizes unnecessary excessive and prolonged exposure of the already sliced Si surface to the etchant solution. This can minimize the already-sliced Si wall's contact time to the etchant to be 1/10~1/100 of the exposure time for the case without the etchant liquid level control, e.g., such as leaving the Si block completely immersed in the etchant during the whole period of Si slicing operation. Such liquid level control of the etchant level can reduce occurrence of undesirable etching and adsorption of contaminants on the already-sliced Si surface.

Figure 12:
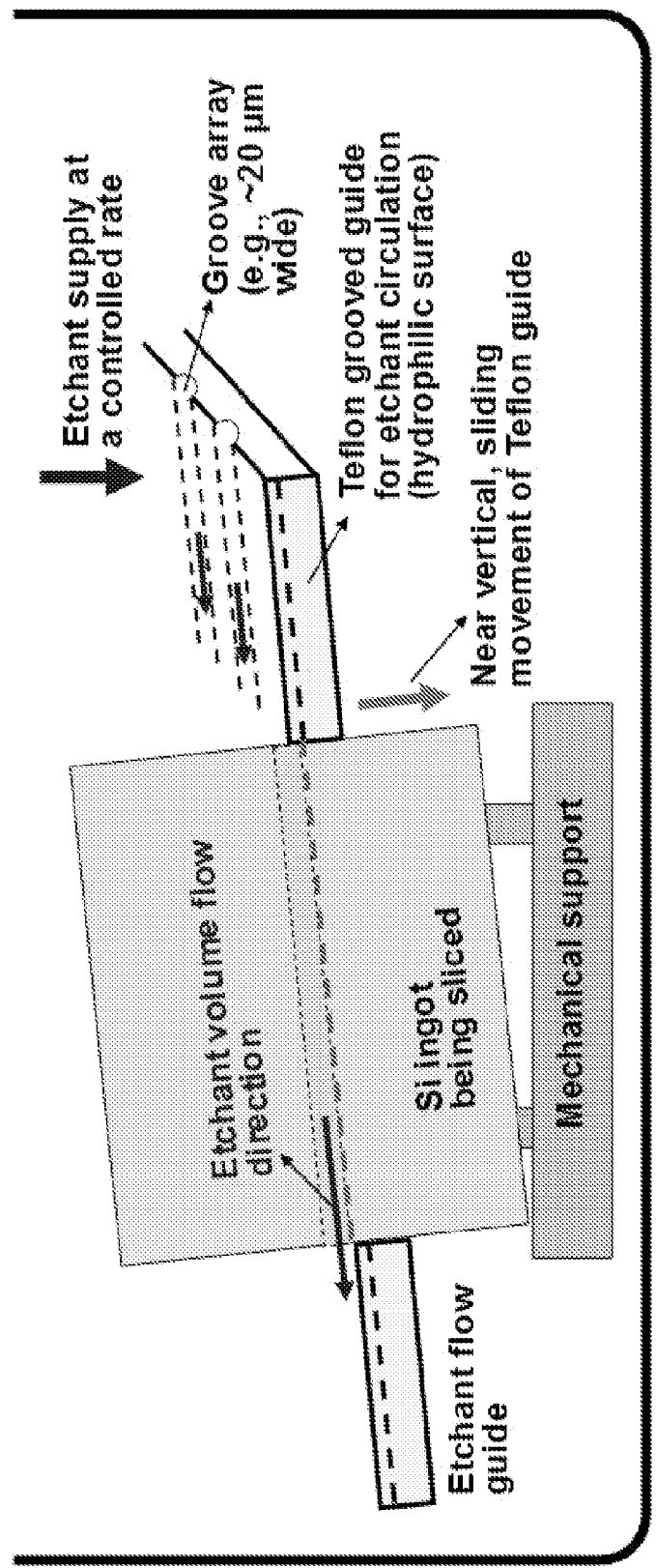
FIG. 12 shows a schematic illustrating a gravity-induced etchant height control process during the exemplary magnetically guided electroless etching process.

FIG. 12 shows a schematic illustrating a gravity-induced etchant height control process during the exemplary magnetically guided electroless etching process. The process shown in FIG. 12 includes implementing a device to control etchant height that utilizes gravity as a means of controlling the etchant height and also provides continuous flow of fresh etchant to the location of the etching near the valley in the Si block being sliced by magnetic guiding (the magnet array is not shown). For example, the device can include a Teflon or other acid-resistant sheet with a parallel array of etchant-guiding groove in a tilt-positioned so as to utilize the gravity to continuously supply the etchant. For example, the exemplary Teflon surface can be converted to become hydrophilic, as in the case of Teflon filters to accommodate the flow of the etchant solution. The height of the etchant level in shown in FIG. 12 is controlled such that the already-sliced Si surface above the etchant liquid level is no longer exposed to the etchant to minimize any contaminations/staining from the acid, and also to minimize any inadvertent etching and widening of the etched slots. Furthermore, modified liquid circulating systems utilizing more active control of low pressure, slow pushing or slow suction of etchants can also be implemented.

The exemplary Si slicing techniques can use dilute HF-based solution as to not introduce as much contaminants to adhere to the sliced Si surface. For example, the Fe in the catalyst etch line dissolves completely in HF, and Au does not chemically react at all with Si or HF solution near room temperature. In the exemplary case that any contaminants stick to the Si surface, a dilute KOH solution rinse can be used to quickly dissolve away a thin layer of Si (for example, 100 nm thickness) together with the associated contaminants.

In some exemplary implementations, the noble metal gold is utilized in the etcher layer and/or protective layer for Si slicing as the catalyst for etching Si by the dilute HF solution. Yet, gold is an expensive material. However, based on the described rough estimates of the amount of the gold needed for the chemical slicing, the amount of gold used for each wafer sliced (e.g., 15.6×15.6 cm area wafer, with a 20 micrometer kerf loss) is ~1.3 microgram per wafer. At the current gold price, the cost of gold catalyst used for each Si wafer slicing amounts to be rather trivial (e.g., less than a few dollars per each Si ingot slicing if there are 10,000 parallel slicings performed per ingot). Furthermore, gold can easily be recovered/collected and recycled after Si slicing. Thus, the use of gold or any other nobel metals as a catalyst is not an inhibiting factor for industrial applications of the disclosed techniques for Si wafer slicing.

FIGS. 13A-13C show schematics of various magnet positions for the exemplary magnetically guided electroless etching process. Each of the described exemplary configurations include their own advantages with respect to applying the maximum magnetic force balanced against the most convenient or most inexpensive processing schemes.

As shown in FIG. 13A, a permanent magnet 1306 (or in other examples, an electromagnet) can be vertically positioned such that its N pole is directly under a container 1301 containing an ingot 1303 by a mechanical support 1304 in an etchant solution 1302. For example, the permanent magnet can be vertically positioned under the ingot 1303 to provide a magnetically attractive pull force on the composite etching structure deposited on the ingot 1301 (e.g., configured as a magnetic etch line array on the top surface of Si block ingot, not shown). For example, the level of the etchant solution 1302 in the container 1301 (e.g., such as a Teflon bath) can be controlled to be lowered in sync with the slicing speed.

As shown in FIG. 13B, the permanent magnet 1306 (or in other examples, an electromagnet) can be vertically positioned such that its S pole is directly above the container 1301 containing the ingot 1303 by the mechanical support 1304 in the etchant solution 1302. In this exemplary configuration, the magnet 1306 (or electromagnet) pushes the composite etching structure (e.g., magnetic etch lines) downward by magnetic repulsion. In this exemplary case, the composite etching structure are configured to be high coercive force permanent magnet films, e.g., pre-magnetized to the same polarity as the magnet pole that faces the magnetic etching structure. For example, the level of the etchant solution 1302 in the container 1301 (e.g., such as a Teflon bath) can also be controlled to be lowered in sync with the slicing speed.

As shown in FIG. 13C, two permanent magnets 1306 (or in other examples, electromagnet poles) can be laterally positioned so that the vertical gradient field pulls the composite etching structure (e.g., magnetic etch lines) on the ingot 1303 downward by magnetic repulsion. In this exemplary implementation, the container 1301 contains the ingot 1303 by the mechanical support 1304 in the etchant solution 1302, and the level of the etchant solution 1302 in the container 1301 (e.g., such as a Teflon bath) can also be controlled to be lowered in sync with the slicing speed.

The disclosed material slicing and shaping technology can be useful for a variety of Si-related technologies including solar cells, electronics applications, three-dimensional circuit interconnections, thin wafers for flexible Si circuits such as compliant displays and biomedical circuit implants. Exemplary applications are described below.

For example, in some implementations, the disclosed technology can be employed to fabricate surface-sliced Si or nanowire-shaped Si arrays for use in photovoltaic solar cells. For example, for efficient photovoltaic solar cell applications, it is highly desirable to have large surface area, as well as sufficient light absorption with minimal sunlight reflectance. The use of thinner Si wafers, e.g. on the order of 10-40 µm thick, for photovoltaic solar cells and Si electronic devices can significantly reduce the Si materials usage, e.g., as compared to the standard 250 µm thick Si wafers. For example, such thin Si wafers tend to be more fragile and hence require careful handling. While there are various possible engineering approaches of handling thin wafers (e.g., with an array of vacuum suction structures) for safe handling and automated mechanical/electrical connection assembly, an alternative approach is to avoid such handling of thin wafers altogether, by utilizing intentional incomplete slicing, e.g., by leaving some base Si material intact and not slicing all the way through, as shown in FIGS. 14-16.

Figure 14A:
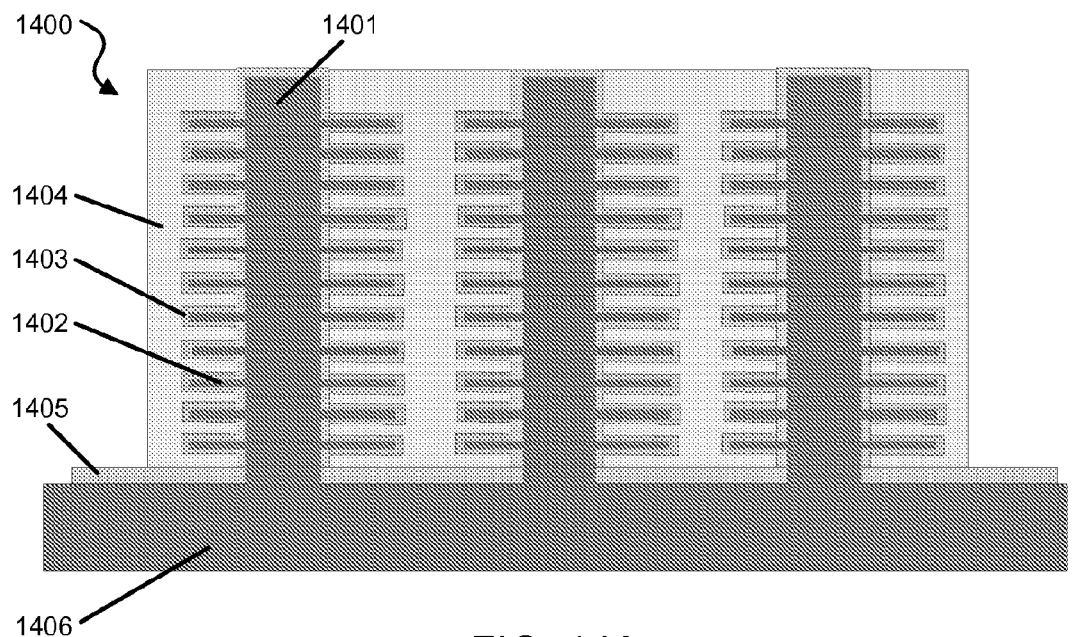
FIG. 14A shows a schematic of an exemplary solar cell array fabricated by the disclosed magnetically guided electroless etching techniques.
Figure 15:
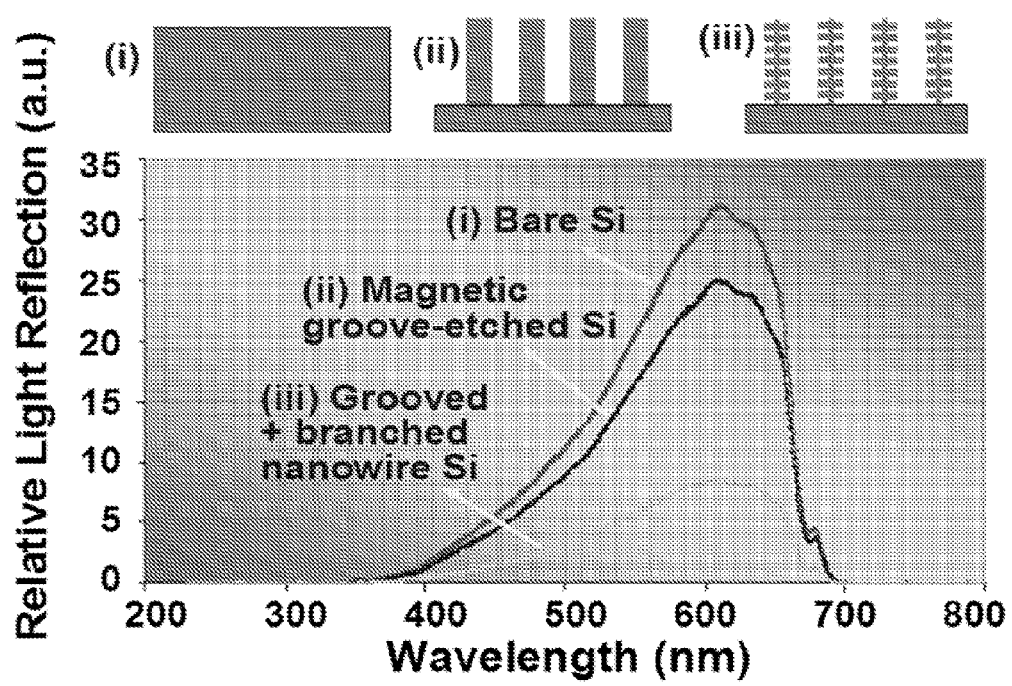
FIG. 15 shows a data plot of the comparative light reflectivity measurements on silicon based structures.

FIG. 14A shows a schematic of a solar cell array 1400 fabricated by the exemplary magnetically guided electroless etching technique. The solar cell array 1400 includes a substrate base material 1406, which can be a Si base, with a thin oxide layer 1405 (e.g., shown as $SiO_2$ in this exemplary solar cell array device). The solar cell array 1400 includes parallel sliced vertical structures 1401 (e.g., configured as n-type Si slices) produced from a magnetically sliced Si micro-sheet array using the disclosed techniques. The parallel sliced structures 1401 include horizontal surface nanoscale branches 1402 (of the same material as the parallel sliced structures 1401, in this exemplary case, n-Si) having a coating 1403 (e.g., configured as p-type Si), which can be added for increased p-n junction surface area to enhance the solar cell reaction and to improve light absorption. For example, the coating 1403 can be coated using plasma enhanced chemical vapor deposition (PECVD) or diffusion techniques. The parallel sliced structures 1401 can be planarized, as shown in the planarized structure 1404, e.g., for top TCO and interconnects.

Figure 14B:
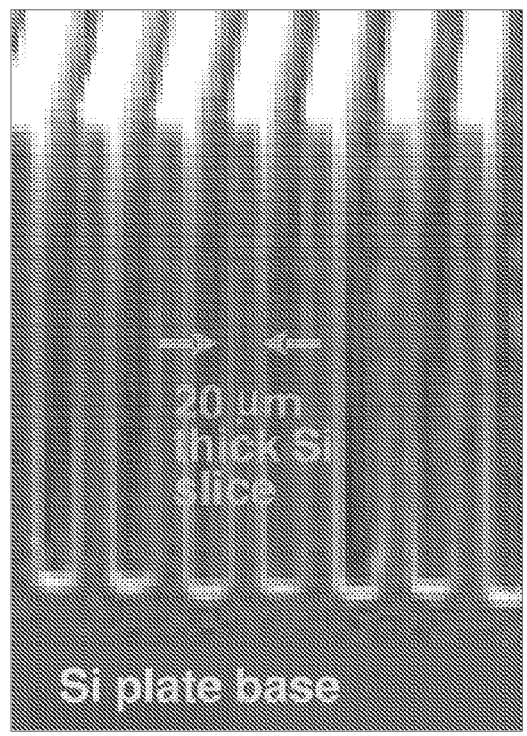
FIG. 14B shows an SEM image of an exemplary parallel sliced Si layer array for substrate-supported vertical solar cell array structure.

FIG. 14B shows an SEM image of an exemplary parallel sliced Si layer array (e.g., thin, 20 µm wide, and not through-cut) for substrate-supported vertical solar cell array structure. For example, the slicing was halted before the through-cut all the way so as to retain some of the bottom base Si material to serve as a support for the vertically positioned, parallel Si slices. Such micrometer dimension Si vertical arrays can be utilized for viable photovoltaic solar cells, e.g., with enhanced sunlight collection (more light absorption). In some implementations, the vertical Si microsheets can also be subjected to additional processing to introduce lateral (horizontal) branches to further increase the surface area and the p-n junction solar reaction area. The surface of the p-type (or n-type) Si vertical sheets (e.g., 20 µm thick) of FIG. 14B (and schematically shown in FIG. 14A) can be coated with n-type (or p-type) Si using PECVD deposition to form the p-n junction. For example, such a 3D geometry could produce a higher solar cell efficiency due to the increased light absorption in the topologically non-flat surface and possibly increased p-n junction area.

For example, the Si microsheet sidewall surfaces shown in FIGS. 14A and 14B can simultaneously and uniformly electroless chemical etched to form a dense array of Si nanowires horizontally protruding perpendicular to each of the sliced Si plates in the array. Electroless chemical etching (e.g., without magnetic guiding in this exemplary case) using $AgNO_3$ type solutions to form Si nanowires can be performed. The composition of the etchant solution used can include, for example, 4.6M HF to 0.02M $AgNO_3$ (v/v=1/1). After submerging the sample for about 20 minutes in the exemplary etchant solution and washing silver reaction dendrites attached to the silicon surface in $HNO_3/H_2O$ solution, the etched sample can be cleaned with deionized water. For example, with such a high density of Si nanowires, a large surface area becomes available on the side wall surface of the vertically sliced and positioned Si microsheet array.

Alternatively, for example, magnetic-guided chemical etching can be utilized to create more controlled, larger diameter horizontal branch Si micropillars, exemplified in FIG. 14B. By using the described Swiss-cheese-shaped mask deposition process of catalytic films (e.g., of Au or Ag) on the side walls of vertical Si slices 1401 (shown in FIG. 14A) using the described template method, more desirable, non-nano side branches can be created. The magnetic field direction applied during Si wire array fabrication can be configured to be perpendicular to the vertical array Si microsheets. The effectiveness of the Swiss-cheese-shaped composite etching structure (e.g., Au/Fe/Au trilayer) has been demonstrated herein for formation of magnetically oriented, tall Si pillar arrays.

FIG. 15 shows a data plot of the comparative light reflectivity measurements on silicon based structures including (i) flat Si, (ii) parallel-wall sliced, vertical Si layer array secured on a remaining, uncut Si substrate, and (iii) sliced Si walls with additionally etched side branches of Si nanowires (e.g., having ~10 nm diameter, ~1 µm long). As shown in the data plot, the use of side branches to the vertical Si microsheet array substantially increases the sunlight absorption and usage due to the much reduced light reflectivity. The sliced (grooved) Si microsheet array structure (ii) reduced the light reflectivity, which is further reduced when the sidewall branch Si was introduced in the sliced Si walls with side branches of Si nanowires structure (iii).

Figure 16A:
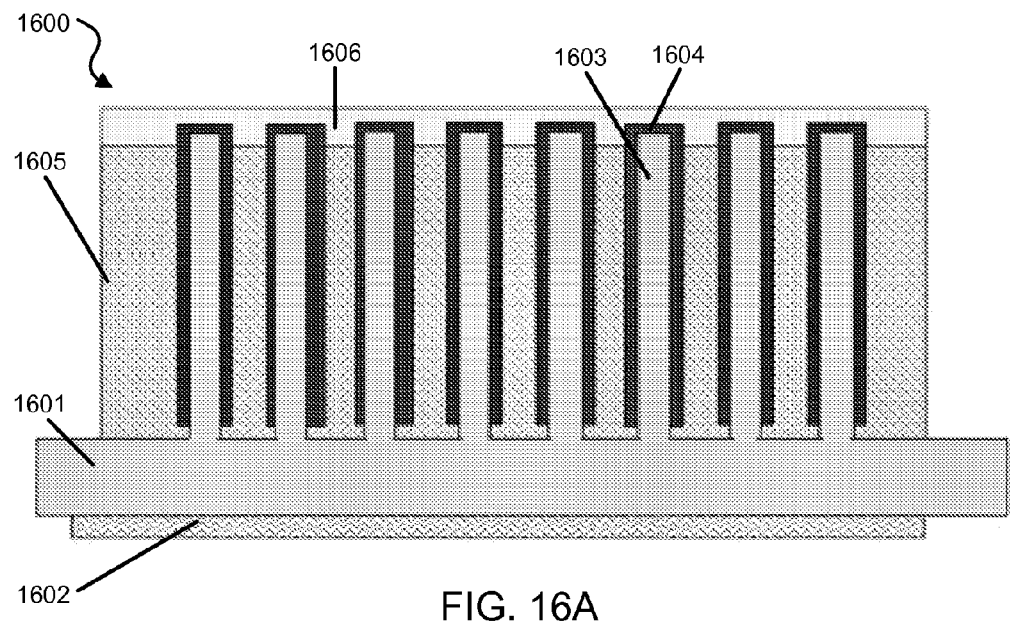
FIG. 16A shows a schematic illustration of an exemplary three-dimensional array of photovoltaic solar cells produced using the disclosed magnetically guided electroless etching techniques.

FIG. 16A shows a schematic illustration of a three-dimensional array of photovoltaic solar cells 1600 produced using the disclosed magnetically guided electroless etching techniques. The solar cell array device 1600 includes a substrate base material 1601, which can be a Si base, coupled to a metallic layer 1602 (e.g., such as aluminum). In some implementations, the solar cell array device 1600 can include a thin oxide layer (e.g., not shown in FIG. 16A, but can be configured as $SiO_2$ in the exemplary case of a Si base material 1601). The solar cell array 1600 includes parallel sliced vertical microsheet or micropillar structures 1603, e.g., configured as p-type Si slices, produced from a magnetically sliced Si micro-sheet array using the disclosed techniques. The parallel sliced vertical microsheet or micropillar structures 1603 include a coating 1604, e.g., configured as a n-type Si, which can be added for increased p-n junction surface area to enhance the solar cell reaction and to improve light absorption. For example, the coating 1604 can be coated using plasma enhanced chemical vapor deposition (PECVD) or diffusion techniques. The parallel sliced vertical microsheet or micropillar structures 1603 can be planarized, e.g., by hydrogen silsesquioxane (HSQ) to provide a $SiO_2$ or other filler material, as shown in the planarized structure 1605. The top surface of the solar cell array device 1600 can be coated with a coating 1606 (e.g., of indium tin oxide (ITO), ZnO, graphene, carbon nanotube networks, or other transparent materials), e.g., to produce transparent conducting oxide (TCO) electrodes and interconnects. For example, the array can be planarized, e.g., filling the space with a HSQ resist, drying, curing and hardening, so as to enable the positioning of optically transparent upper electrode layer, using a transparent oxide filler space between neighboring nano solar cells. For example, optional light reflecting nano or microspheres may be utilized for enhanced light collection. Other structures, including dielectric layers, anti-reflection layers, etc., can be included in the solar cell array device 1600 that are not shown in the exemplary schematic of FIG. 16A.

Micrometer dimension Si vertical arrays could be utilized for viable photovoltaic solar cells if properly configured, e.g., with enhanced sunlight collection (more light absorption). For example, because of the 3D nature of the non-through-cut Si slice vertical array of FIG. 16A, it can be difficult to place the upper TCO electrode (e.g., such as an ITO conductive layer) directly above the exemplary Si parallel sliced vertical microsheet or micropillar structures 1603. Thus, a planarization process can be employed inserting a transparent filler material (e.g., such as $SiO_2$) to the empty space between the vertical Si layers so as to allow the blanket deposition of the transparent conducting layer such as the transparent conducting oxide. For example, an exemplary planarization technique can include spin coating or dip coating hydrogen silsesquioxane (HSQ) resist liquid (or Si-containing sol-gel precursor liquid) to fill the valley regions, curing, drying and reactive ion etch (RIE) to remove the overfilled excess thickness regions to the desired planarized height so as to expose the top of the Si solar cell electrodes, then baking at 110° C. to convert the resist to the $SiO_2$ material.

Figure 16B:
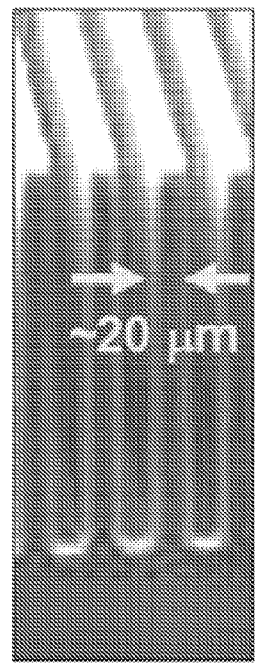
FIGS. 16B and 16C show SEM micrographs of microsheets and micropillars produced using the disclosed magnetically guided electroless etching techniques.
Figure 16C:
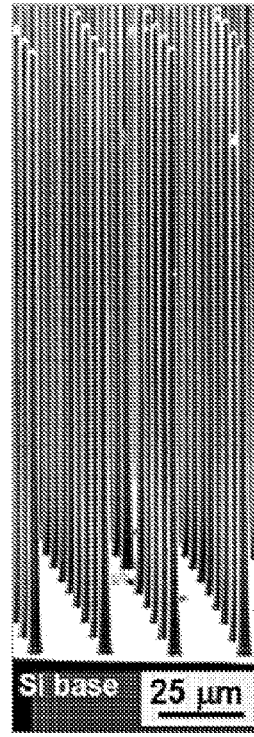

FIGS. 16B and 16C show SEM micrographs of microsheets and micropillars produced using the disclosed magnetically guided electroless etching techniques. Microwire array solar cell assembly can be an effective solar cells using a relatively small amount of Si semiconductor material.

In another aspect, the disclosed technology includes processes of implementing the disclosed Si sliced nano-/microsheet and nano-/micro-pillar array devices produced using the described magnetically guided chemical etching techniques in biological applications.

Living cells can be modified by physical approaches for various purposes. For example, such approaches include cellular injections for drug delivery, gene therapy, and other types of cellular manipulation used in drug discovery and research, and ultimately clinical applications, for a deeper understanding of human development and disease. Single-cell transfection using nanoscale tips (e.g., carbon nanotube tips) can be implemented using existing techniques (e.g., AFM-based systems), but multi-cells transfection using long needle arrays comparable to cell dimensions (e.g., ~50 µm height) remain a challenge. Other existing techniques include manual microinjection using a single glass pipette remains the most popular, however other techniques have been developed including viral vectors, electroporation, liposomal carriers, and laser trapping among others. Even though these methods have merit, each of them includes short-comings making them less attractive for cellular injections, particularly for multiple injections in parallel. Some of the common disadvantages to the existing methods include cell damage, loss in viability, increased waste and loss of effectiveness of delivering materials.

One of the many exemplary advantages of the magnetic-guided Si etching includes its ability to fabricate very tall, high-aspect-ratio Si micro-needles, e.g., as tall as ~200 μm tall with only a few μm in diameter. The disclosed microneedles are mechanically more compliant due to their small dimension. Also, for example, the exemplary microneedles can also be coated with an inert metal (Au, Pt) or bioactive metal for enhanced mechanical toughness and easy conjugation and attachment of biomolecules. The exemplary metallic microneedles can also be fabricated using the Si microneedles as the template. The disclosed microneedle technique provides a new approach for genetic manipulations, e.g., by which specific proteins can be synthesized. For example, as the cell commands via signal pathway is affected/decided by specific proteins, the gene delivery into cell interior using Si microneedles of the disclosed technology can be useful in implementation. For example, a simple endocytosis of biomolecules to cell interior is not desirable since such endocytosed materials are confined to small membrane-bounded vesicles such as endosomes, and then later moved/sequestered into lysosomes and decomposed by enzymes. Therefore, a direct insertion into the cell cytoplasm or nucleus is beneficial.

A living cell's size is typically 5- or 10-50 μm, but can vary based on cell type and other factors. The exemplary Si microneedles can poke into the cells and deliver the biological entity, but they need to be tall to successfully implement a desired application. The disclosed technology includes methods to produce exemplary microneedles with a diameter that can be configured to be small to effectively implement the application, e.g., since the larger the needle size is, the more adverse damages the cells experience. In some examples, the tip of the microneedles can be sharpened to 30 nm diameter with a gradual change in diameter with the needle height. Si microneedles with a large aspect-ratio of the can be produced on a substrate base with a large area, for example, 10 cm×10 cm area. This exemplary area is large enough to contain ~1 million living cells, onto which biomolecules and genetic components can be inserted to modify these cells simultaneously.

Bio-substances including, but not limited to, various proteins, RNA, DNA, quantum dots, nanoparticles, etc., can be injected by nano/micro-needles for cell therapy protocols, with emphasis on the delivery of nucleic acids, including short interfering RNAs (siRNAs). For example, normal genes can be (i) inserted into the human cells and biological tissue to replace an abnormal disease causing genes (gene therapy) or (ii) introduce genes to re-engineer the fate of the cells in the case of stem cells or in the process of creating iPS cells (e.g., induced pluripotent stem cells from the patient's own non-pluripotent cells such as skin cells by a forced expression of genes). This type of nanoneedle array can be produced implementing the disclosed technology, and be especially beneficial for many cell types including primary cells, neurons, stem cells, and white blood cells, among others, for example. Some example molecules that can be inserted into cells using the exemplary tall Si pillar arrays include, but are not limited to, siRNA or fluorescent molecules (such as a green fluorescent protein). As there is a strong need for this type of cell transfection devices, multi-billion dollar business can benefit from the new Si slicing and shaping technology.

Figure 17:
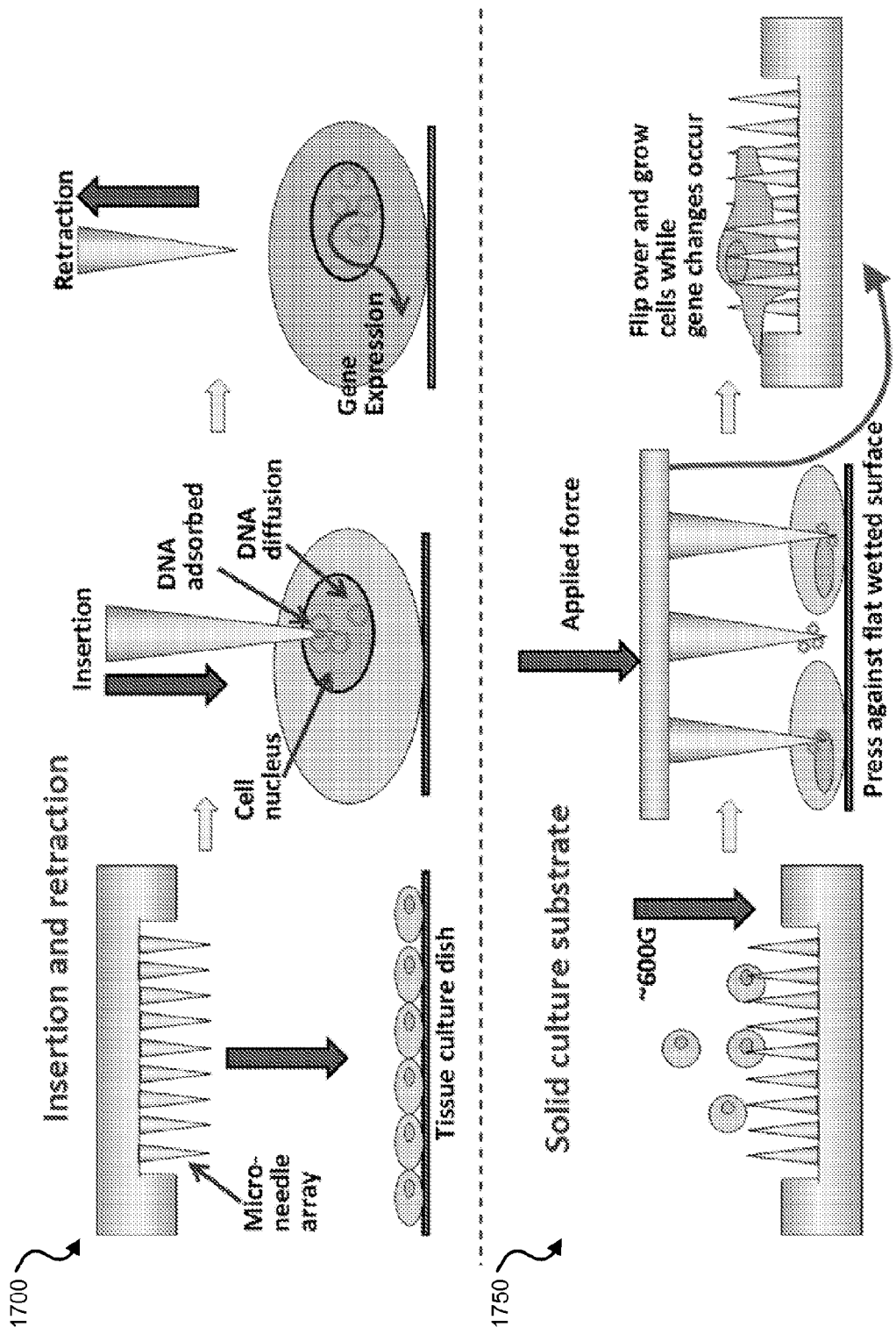
FIG. 17 shows a schematic illustration of processes for cell puncturing into a multi-cell array using exemplary Si nano-/micro-needles produced using the disclosed magnetically guided etching techniques.

FIG. 17 shows a process 1700 and a process 1750 for cell puncturing into multi-cell array using the exemplary tall Si nanoneedles or microneedles produced using the disclosed magnetically guided etching techniques, in which the exemplary nano- or micro-needles include functionalized tips for delivery of intended biomolecules or other agents for cell modifications. As shown in FIG. 17, the exemplary nano- or micro-needle array performs four main functions for to function as a cellular injection device including: (i) the adhesion/attraction of payload molecules to the nano-needles; (ii) the piercing of the target cells by the nano-/micro-needles without cellular damage, (iii) release of the payload molecules inside the target cells; and (iv) the retraction of the nano-/micro-needles from the cells without the loss of viability. One exemplary advantage to the tall pillar structure is an added option of using the nano-/micro-needle array with the needles pointing upward, and to use them as a tissue engineering construct, with the cells growing on top of the needles. The nano-needle array can be utilized for retraction after release or growth of the cells on the needle-array. Exemplary implementations were performed to test this nano-needle, e.g., including the adsorption of green fluorescent protein (GFP) DNA electrostatically attached on the surface of the nano-needle tip.

FIG. 17 shows the process 1700 for specific targeting and piercing of the nucleus of cells for gene expression or other applications. For example, the cells can include human mesenchymal stem cells (MSCs) grown on tissue culture surfaces (e.g., in 10% fetal bovine serum growth media, 5% $CO_2$ humidified incubator at 37° C.). An inverted microscope and x-y-z manipulator can be implemented control the positioning of an exemplary micro-/nano-needle array of the disclosed technology. The exemplary needle array can remain inserted in the cell nucleus for a few minutes, or other time duration desired, to allow for the diffusion of the DNA from the surface of the needle into the nucleus. Subsequently, the needles can be extracted.

The process 1750 for using the needle array can be implemented where the cells are gently forced against the needles. In this exemplary process, cells can have nucleic acids (e.g., DNA, RNA), proteins, or imaging molecules inserted and then the cells are grown on the surface of the array. First, the cells can be obtained in a suspension and gently centrifuged downward on top of the needle array. Then, the cells can be sandwiched in-between a flat wetted surface and the needle array to gently press the cells so as to penetrate the needles into the cell cytoplasm. Finally, the array can be turned with the needles facing upward to allow for subsequent growth and gene expression. The array can serve to provide a mechanical and stimulating support. The nano-topographical features of the exemplary nanostructures produced using the disclosed techniques can be structured as nanorods, nanogrooves, nanotubes, nano-needles to have enhanced culture effects on cells.

In another aspect, the disclosed technology includes a method for magnetically guided electroless etching. The method includes forming line, rectangle, circle, or irregular patterns on a substrate using lithographic techniques selected from photolithography, deep UV lithography, extreme UV lithography, nano-imprint lithography. The method includes depositing at least one magnetic metal layer and one noble metal layer, or a sandwich composite comprising layers of (noble metal or alloy)-(magnetic metal or alloy)-(noble metal or alloy) on the substrate having the formed patterns, in which the depositing uses one of a thermal evaporation, sputtering, chemical vapor deposition, electroplating or electroless plating process. The method includes dipping or immersing the substrate having the formed patterns and deposited layers into a container holding a mixture chemical etching solution. The method includes slicing the silicon substrate by performing magnetically guided electroless etching.

In another aspect, the disclosed technology includes a method for slicing a silicon substrate. The method includes forming patterns of a transparent thermoplastic resist layer on a silicon substrate comprising pressing a line patterned mold on the transparent thermoplastic resist layer disposed on the silicon substrate under predetermined temperature and pressure, e.g., in which the transparent thermoplastic comprises poly(methyl methacrylate) (PMMA) or poly(methyl 2-methylpropenoate). The method includes removing remaining transparent thermoplastic resist layer pressed by the mold using an oxygen reactive-ion etching process. The method includes depositing three metal layers comprising Au—Fe—Au layers on the silicon substrate having the formed patterns using a thermal evaporation process. The method includes dipping or immersing the silicon substrate having the formed patterns and deposited Au—Fe—Au layers into a container holding a mixture solution of hydrofluoric acid and hydrogen peroxide ($HF/H_2O_2/H_2O$) at room temperature. The method includes slicing the silicon substrate by performing magnetic electroless etching. The method includes removing the formed patterns of the transparent thermoplastic resist layer and the deposited three metal layers from the sliced silicon substrate.

For example, implementations of the method for slicing a silicon substrate can include performing magnetic electroless etching that includes positioning a permanent magnet in a bottom area of the container to supply directionally attractive force pulling ferromagnetic Fe layers sandwiched between two Au catalyst layers. Also, for example, implementations of the method for slicing a silicon substrate can include mirror polishing one side of the silicon substrate and cutting the silicon substrate from a wafer.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A method for guided electroless etching to form a cut in a material, comprising:
   forming a patterned mask on a substrate to partially cover the surface of the substrate while exposing one or more selected regions on the surface of the substrate to be removed by etching;
   depositing an etcher layer of a first catalyst material on each exposed surface of the selected regions of the substrate, a guide layer of a magnetic material on the etcher layer, and a protection layer of a second catalyst material on the guide layer, wherein the etcher layer, guide layer and protection layer form a composite etching structure;
   etching the substrate by applying an etching solution to the substrate that chemically reacts with the etcher layer and etches material from the substrate at each selected region not covered by the patterned mask to form a sliced region;
   steering the composite etching structure into the substrate during the etching by an applied magnetic field that creates a force on the guide layer to direct a direction of the etching, wherein the steering defines the shape of the sliced region of the etched substrate; and
   removing the etched material, the patterned mask, and the composite etching structure from the substrate to produce a sliced material structure.

2. The method of claim 1, wherein the forming the patterned mask includes depositing a resist layer to form the mask using lithographic techniques selected from photolithography, deep ultraviolet (UV) lithography, extreme UV lithography, nano-imprint lithography, ink jet printing lithography, shadow mask patterning, or electron beam lithography.

3. The method of claim 1, wherein the depositing the etcher layer, the guide layer, and the protection layer includes using one of thermal evaporation, sputtering, ion beam deposition, pulsed laser deposition, chemical vapor deposition, electroplating, or electroless plating processes.

4. The method of claim 1, wherein the etching solution includes at least one of hydrofluoric acid (HF), hydrogen peroxide ($H_2O_2$), nitric acid ($HNO_3$), ammonium fluoride ($NH_4F$), water ($H_2O$), sodium hydroxide (NaOH), or potassium hydroxide (KOH).

5. The method of claim 1, wherein the applying the etching solution includes immersing the substrate having the formed pattern and deposited layers into a container containing the etching solution.

6. The method of claim 5, comprising controlling the level of etching solution in the container.

7. The method of claim 1, wherein the applied magnetic field produces a magnetostatic attractive force on the magnetic material that accelerates a descending speed of the first catalyst material to etch the substrate.

8. The method of claim 1, wherein the sliced region is formed along an axis not aligned with the crystallographic orientation of the substrate.

9. The method of claim 1, wherein the first and second catalyst materials include at least one of gold (Au), Au-containing alloy, platinum (Pt), Pt-containing alloy, palladium (Pd), Pd-containing alloy, silver (Ag), or Ag-containing alloy.

10. The method of claim 9, wherein the first catalyst material and the second catalyst material are the same material.

11. The method of claim 1, wherein the magnetic material includes at least one of iron (Fe), Fe-containing alloy, cobalt (Co), Co-containing alloy, nickel (Ni), or Ni-containing alloy.

12. The method of claim 1, wherein the magnetic material includes at least one of a CoPt intermetallic compound, FePt intermetallic compound, CoPd intermetallic compound, Sm—Co permanent magnet alloy, Nd—Fe—B permanent magnet alloy, or ferrite oxide magnet.

13. The method of claim 1, wherein the etcher layer and the guide layer include a relative geometry selected from a hidden magnetic layer sandwich configuration, enveloped magnetic layer configuration, embedded island magnetic material configuration, or porous catalyst and porous magnetic material layered configuration.

14. The method of claim 1, wherein the substrate includes at least one of silicon or germanium.

15. The method of claim 1, wherein the pattern includes line patterns, rectangle patterns, circular patterns, curved patterns, or irregular patterns.

16. The method of claim 1, wherein the sliced material structure is formed of silicon and includes a thickness of 5 µm or less, wherein the silicon sliced material structure is a flexible material.

17. The method of claim 16, wherein the sliced material structure is implemented in a device including one of a flexible display, a sensor, or an actuator.

18. The method of claim 1, wherein the composite etching structure includes pores in each of the etcher layer, the guide layer, and the protection layer such that the sliced region is etched with an increased depth.

19. The method of claim 18, wherein the sliced region of the sliced material structure forms needle or pillar structures of a diameter of 10 µm or less and a height of 300 µm or greater.

20. The method of claim 19, wherein the sliced material structure is implemented in a device including one of a solar cell, a sensor probe, or a battery electrode.

21. The method of claim 1, wherein the sliced region is completely etched through the substrate to produce a plurality of uncoupled sliced material structures.

22. The method of claim 1, wherein the sliced region is partially etched into the substrate to produce an array of aligned pillar or sheet structures.

23. The method of claim 22, wherein the sliced material structure including the aligned pillar or sheet structures is implemented in a device including a photovoltaic solar cell structure, the photovoltaic solar cell structure comprising a doped surface over the aligned pillar or sheet structures to provide photovoltaic reactions, and an optically transparent planarized filler material between adjacent aligned pillar or sheet structures.

24. The method of claim 23, wherein the photovoltaic solar cell structure further comprises an optically transparent conducting oxide on an upper surface, and electronic circuitry on the optically transparent conducting oxide.

25. The method of claim 1, wherein the applying the etching solution includes tilting the substrate having the formed pattern and deposited layers and pouring the etching solution over the tilted substrate with a controlled pour rate.

26. The method of claim 25, wherein the etching solution includes a depth above the upper surface of the sliced region of less than 5 mm.

27. The method of claim 1, wherein the applied magnetic field is generated by one of a magnet or electromagnet.

28. The method of claim 27, wherein the magnet or electromagnet is positioned above the substrate and the force is a repulsive force that pushes the composite etching structure into the substrate during etching.

29. The method of claim 27, wherein the magnet includes two laterally positioned magnets.

30. The method of claim 27, wherein the electromagnet includes two laterally positioned electromagnets.

31. A method for guided electroless etching to slice and shape a material, comprising:
forming a patterned mask on a substrate to partially cover the surface of the substrate while exposing one or more selected regions on the surface of the substrate to be removed by etching;
depositing an etcher layer of a first catalyst material on each exposed surface of the selected regions of the substrate, a guide layer of a magnetic material on the etcher layer, and a protection layer of a second catalyst material on the guide layer, wherein the etcher layer, guide layer and protection layer form a composite etching structure;
etching the substrate by applying an etching solution to the substrate that chemically reacts with the etcher layer and etches material from the substrate at each exposed region not covered by the patterned mask to form a sliced region;
steering the composite etching structure into the substrate during the etching by an applied magnetic field that creates a force on the guide layer to direct a direction of the etching, wherein the steering includes changing the direction by altering the applied magnetic field direction during the etching to define a curved or zigzag shape of the sliced region of the etched substrate; and
removing the etched material, the patterned mask, and the composite etching structure from the substrate to produce a sliced material structure including curved or zigzag nanowire structures on a base of the sliced material structure.

32. The method of claim 31, wherein the zigzag nanowire structures includes a tapered diameter increasing towards the substrate.

33. The method of claim 31, wherein the sliced material structure is implemented in a device including one of a solar cell, a sensor probe, anti-reflection coating, piezoelectric or a compliant interconnect.

34. A method for guided electroless etching to slice a material, comprising:
forming a pattern on a substrate by a mask that at least partially covers the surface of the substrate;
depositing an etcher layer of a first catalyst material on the surface of the patterned substrate and a guide layer of a magnetic material on the etcher layer to form a composite etching structure, wherein the depositing further comprises depositing a protective layer that couples with the etcher layer to envelope the magnetic layer in the composite etching structure;
etching the substrate by applying an etching solution to the substrate that chemically reacts with the etcher layer and etches material from the substrate at exposed regions not covered by the mask to form sliced regions;
steering the composite etching structure into the substrate during the etching by an applied magnetic field that creates a force on the guide layer to direct a direction of the etching, wherein the steering defines the shape of the sliced regions of the etched substrate; and
removing the etched material, the mask, and the composite etching structure from the substrate to produce a sliced material structure.

35. The method of claim 34, wherein the magnetic layer includes magnetic particles formed in a catalyst material.

36. The method of claim 35, wherein the magnetic layer includes a protective coating.

37. The method of claim 36, wherein the protective coating includes Teflon.

38. The method of claim 34, wherein the composite etching structure includes pores in each of the etcher layer, the guide layer, and the protective layer.

* * * * *